United States Patent
Barnicki et al.

(10) Patent No.: US 10,611,637 B2
(45) Date of Patent: *Apr. 7, 2020

(54) METHOD FOR THE MANUFACTURE OF CYCLODODECASULFUR

(71) Applicant: EASTMAN CHEMICAL COMPANY, Kingsport, TN (US)

(72) Inventors: Scott Donald Barnicki, Kingsport, TN (US); Robert Thomas Hembre, Johnson City, TN (US); Elaine Beatrice Mackenzie, Enfield, CT (US); Joy Lynn Laningham, Erwin, TN (US); Michael Richard Laningham, Erwin, TN (US); Shane Kipley Kirk, Church Hill, TN (US); Larry Wayne Blair, Gate City, VA (US); Sumit Chakraborty, Johnson City, TN (US); Venkateswarlu Bhamidi, Kingsport, TN (US); Guoxiong Hua, Fife (GB); John Derek Woollins, Fife (GB)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/995,574

(22) Filed: Jun. 1, 2018

(65) Prior Publication Data

US 2018/0273382 A1 Sep. 27, 2018

Related U.S. Application Data

(63) Continuation of application No. 15/440,056, filed on Feb. 23, 2017, now Pat. No. 10,011,485.

(60) Provisional application No. 62/302,213, filed on Mar. 2, 2016.

(51) Int. Cl.
  *C01B 17/02* (2006.01)
  *C01B 17/12* (2006.01)
  *C07D 341/00* (2006.01)

(52) U.S. Cl.
  CPC ...... *C01B 17/0253* (2013.01); *C01B 17/0243* (2013.01); *C01B 17/12* (2013.01); *C07D 341/00* (2013.01)

(58) Field of Classification Search
  CPC ... C07D 341/00; C01B 17/0243; C01B 17/12; C01B 17/0253
  See application file for complete search history.

(56) References Cited

U.S. PATENT DOCUMENTS

| | | |
|---|---|---|
| 1,875,372 A | 9/1932 | EndreS |
| 2,419,309 A | 4/1947 | Belchetz |
| 2,419,310 A | 4/1947 | Belchetz |
| 2,460,365 A | 2/1949 | Schallis |
| 2,462,146 A | 2/1949 | Walcott et al. |
| 2,513,524 A | 7/1950 | Schallis |
| 2,534,063 A | 12/1950 | Ross et al. |
| 2,757,075 A | 7/1956 | Haimsohn |
| 3,844,941 A | 10/1974 | Jones |
| 3,891,743 A | 6/1975 | Block |
| 4,017,467 A | 4/1977 | Doss |
| 4,238,470 A | 12/1980 | Young |
| 4,242,472 A | 12/1980 | Hoshino et al. |
| 4,740,559 A | 4/1988 | Johansson et al. |
| 4,752,507 A | 6/1988 | Johansson et al. |
| 4,870,135 A | 9/1989 | Mowood et al. |
| 6,319,993 B2 | 11/2001 | Weidenhaupt et al. |
| 6,420,581 B1 | 7/2002 | Lodaya et al. |
| 6,441,098 B2 | 8/2002 | Halko et al. |
| 6,624,274 B1 | 9/2003 | Suddaby |
| 7,569,639 B2 | 8/2009 | Choi et al. |
| 7,662,874 B2 | 2/2010 | Korth et al. |
| 8,859,719 B2 | 10/2014 | Mohamed et al. |
| 10,011,663 B2 | 7/2018 | Barnicki et al. |
| 10,280,281 B2 | 5/2019 | Barnicki et al. |
| 2014/0020808 A1 | 1/2014 | Watanabe |
| 2014/0116594 A1 | 5/2014 | Miyazaki |
| 2014/0200383 A1 | 7/2014 | Marks et al. |
| 2014/0213708 A1 | 7/2014 | Kushida |
| 2017/0002153 A1 | 1/2017 | Osumi |
| 2017/0253484 A1 | 9/2017 | Barnicki et al. |

FOREIGN PATENT DOCUMENTS

| | | |
|---|---|---|
| CN | 101 837 958 A | 9/2010 |
| CN | 103 601 156 A | 2/2014 |
| EP | 0846722 B1 | 4/2002 |
| EP | 1500630 A2 | 1/2005 |
| EP | 2128153 B1 | 8/2013 |
| WO | WO 2003060002 | 7/2003 |

OTHER PUBLICATIONS

PCT International Search Report and Written Opinion dated Oct. 9, 2018 for International Application No. PCT/US2018/042402.
Kuznetsov, A. A. et al., "Investigation of the process of vulcanization bypolymeric Sulphur in the metastable state", International Polymer Science and Technology, vol. 29, No. 1, Jan. 2002, pp. T/1-3.
Znak, Z.O, et al. Physicochemical Properties of Rubber Compositions Vulcanized by Polymeric Sulfur, Materials Science, vol. 52, No. 3, Nov. 2016, pp. 407-413.
ASTM D1993-03 (2013).
Bueno-Ferrer et al., Journal of Rare Earths, 28, 2010, "Relationship between surface area and crystal size of pure and doped cerium oxides", pp. 647-653.
Chen et al., "Quantitative Analysis of Powder Mixtures by Raman Spectrometry: the influence of particle size and its correction", Analytical Chemistry, 84, 2012, pp. 4088-4094.
Choi et al. "Thermal Aging Behaviors of Elemental Sulfur-Free Polyisoprene Vulcanizates" *Bull. Korean Chem. Soc.*, Col. 26, 2005, pp. 1853-1855.

(Continued)

*Primary Examiner* — Timothy C Vanoy
(74) *Attorney, Agent, or Firm* — Michael K. Carrier

(57) ABSTRACT

The present invention relates to a method for the manufacture of cyclododecasulfur, a cyclic sulfur allotrope wherein the number of sulfur (S) atoms in the allotrope's homocyclic ring is 12. The method includes reacting a metallasulfur derivative with an oxidizing agent in a reaction zone to form a cyclododecasulfur-containing reaction mixture.

18 Claims, No Drawings

(56) References Cited

OTHER PUBLICATIONS

Eckert et al. "Elemental Sulfur and Sulfur-Rich Compounds" *Springer*, 2003, pp. 10-54.
Leste-Lasserre, Pierre "Sulfur Allotrope Chemistry" *McGill University*, 2001, pp. 119-132.
Masamichi Ikeda et al., Radioisotopes, "Measurements of Sulfure Solubility and Diffusibility in Rubber by Tracer Method", vol. 20, No. 10, p. 556, (1973).
Mausle, H.J.; Steudel, R., "Simple preparation of Cyclohexasulfur (S6) from dichlorodisulfane (S2Cl2) and ionic iodides", Z. anorg. allg. Chem. 463, 1980, pp. 27-31.
Steudel, R.; Strauss, R.; Koch, L., "Quantitative HPLC Analysis and Thermodynamics of Sulfur Melts", Angew. Chem. Int. Ed. Engl., 24(1), 1985, pp. 59-60.
Steudel, R..; Mausle, H-J., "Detection of Large-Ring Sulfur Molecules in Liquid Sulfur: Simple Preparation of S12, α-S18, S20 from S8", Angew. Chem. Int. Ed. Engl., 18(2), 1979, pp. 152-153.
Steudel, R.; Eckert, B., "Solid Sulfur Allotropes", Topics in Current Chemistry (2003), 230, pp. 1-79.
Steudel et al., "Infrared and Raman Spectra of Cyclo Dodecasulphur" Journal of Molecular Spectroscopy, 51, 1974, pp. 189-193.
Schmidt, M.; Block, H.-D., "Occurrence of Cyclododecasulfur in Sulfur Melts", Angew. Chem. Int. Ed. Engl., 6(11), 1967, pp. 955-956.
Schmidt, M.; Wilhelm, E., "Cyclodocecasulfur, S12", Angew. Chem. Int. Ed. Engl., 5(11), 1966, pp. 964-965.
Steudel, R.; Steidel, J.; Sandow, T., "Representation, Crystal Structure and Vibrational Spectra of CycloUndecasulfur and Cyclotridecasulfur", Z. Natureforsch B 1986, 41, pp. 958-970.
Schmidt, M.; Knippschild, G.; Wilhelm, E., "Memorandum on a Simplified Synthesis of Cyclododecasulfure $S_{12}$" Chem. Ber., 101 1968, p. 381-382.
Schmidt, M.; Block, B.; Block, H.D.; Kopf, H.; Wilhelm, E., "Cycloheptasulfur, S7, and Cyclodocecasulfur, S10—Two New Sulfur Rings", Angew. Chem. Int. Ed. Engl., 7(8), 1968, pp. 632-633.
Inorganic Chemistry by Duward Shriver, P.W. Atkins and Cooper Langford, W. H. Freeman & Co., 1990, pp. 407-408.
Copending U.S. Appl. No. 15/015,165, filed Feb. 4, 2016, Barnicki, et al. Now U.S. Pat. No. 10,011,663.
Office Action dated Jul. 5, 2016 received in co-pending U.S. Appl. No. 15/015,165.
Office Action dated Jan. 13, 2017 received in co-pending U.S. Appl. No. 15/015,165.
Copending U.S. Appl. No. 15/440,056, filed Feb. 23, 2017, Barnicki, et al. Now Publication No. 2017-0253484.
Copending U.S. Appl. No. 15/440,007, filed Feb. 23, 2017, Barnicki, et al.
Steudel, Ralf, "Elemental Sulfur and Related Homocyclic Compounds and Ions", Studies in Inorganic Chemistry, 1984, v5, p. 3.
PCT International Search Report and Written Opinion dated Mar. 23, 2017 for International Application No. PCT/US2016/067695.
Steudel et al, Thermal Polymerization and Depolymerization Reactions of 10 Sulfer Allotropes Studied by HPLC and DSC, vol. 517, No. 10, pp. 7-42, Oct. 1, 1984.
PCT International Search Report and Written Opinion dated Apr. 19, 2017 for International Application No. PCT/US2017/019881.
Moeckel, Herman, "Separation of dihydrogen polysulfides (polysulfanes) using reversed-phase HPLC", Fresenius' Zeitschrift Fuer Analytische Chemie, vol. 318, No. 2, 1984, pp. 116-120.
Zysman-Colman, Eli et al., "Probing the chemistry of rare sulfur allotropes: S9, S12 and S20", Journal of Sulfur Chemistry, vol. 29, No. 3-4, 2008, pp. 309-326.
PCT International Search Report and Written Opinion dated May 11, 2017 for International Application No. PCT/US2017/019888.
Office Action dated Jun. 30, 2017 received in co-pending U.S. Appl. No. 15/015,165.
Copending U.S. Appl. No. 15/659,094, filed Jul. 25, 2017, Barnicki et al.
Office Action dated Nov. 22, 2017 received in co-pending U.S. Appl. No. 15/440,007.
Office Action dated Nov. 24, 2017 received in co-pending U.S. Appl. No. 15/440,056.
Buskirk, P.R. Van, et al, Practacle Parameters for Mixing, Rubber Chemistry and Technology, vol. 48, pp. 577-591, May 1975.
Kim, Pan Soo, et al, Flow Visualization of Intermeshing and Separated Counter-Rotating Rotor Internal Mixer, Rubber Chemistry and Technology, vol. 67, pp. 880-891, Apr. 1994.
Manas-Zloczower, I. et al, Dispersive Mixing in Internal Mixers—A Theoretical Model Based on Agglomerate Rupture, vol. 55, pp. 1250-1285, 1982.
Notice of Allowance dated Mar. 20, 2018 received in co-pending U.S. Appl. No. 15/440,056.
Notice of Allowance dated Mar. 26, 2018 received in co-pending U.S. Appl. No. 15/440,007.
Notice of Allowance dated May 3, 2018 received in co-pending U.S. Appl. No. 15/015,165.
Office Action dated May 3, 2018 received in co-pending U.S. Appl. No. 15/659,094.
Copending U.S. Appl. No. 15/991,122, filed May 29, 2018, Barnicki et al.
Office Action dated Aug. 27, 2018 received in co-pending U.S. Appl. No. 15/991,122.
Copending U.S. Appl. No. 16/123,591, filed Sep. 6, 2018, Barnicki et al.
Notice of Allowance dated Dec. 21, 2018 received in co-pending U.S. Appl. No. 15/659,094.
Steudel, Ralph et al, "A New Allotrope of Elemental Sulfur: Convenient Preparation of cyclo-S 14 from S 8", Angew. Chem. Int. Ed., Jan. 1, 1998, pp. 2377-2378.
Office Action dated Mar. 7, 2019 received in co-pending U.S. Appl. No. 15/991,122.
Copending U.S. Appl. No. 16/358,078, filed Mar. 19, 2019, Barnicki et al.
Notice of Allowance dated Jun. 24, 2019 received in co-pending U.S. Appl. No. 15/991,122.

METHOD FOR THE MANUFACTURE OF CYCLODODECASULFUR

CROSS-REFERENCE TO RELATED APPLICATIONS

This application is a continuation of U.S. patent application Ser. No. 15/440,056 filed on Feb. 23, 2017, which claims the benefit of U.S. Provisional Patent Application Ser. No. 62/302,213 filed on Mar. 2, 2016, the disclosures of which are incorporated herein by reference in their entirety.

PARTIES TO JOINT RESEARCH AGREEMENT

Inventions disclosed or claimed herein were made pursuant to a Joint Research Agreement between Eastman Chemical Company and the University Court of the University of St. Andrews, a charitable body registered in Scotland.

FIELD OF THE INVENTION

The present invention relates generally to a method for the manufacture of a cyclic sulfur allotrope, and specifically cyclododecasulfur, wherein the number of sulfur (S) atoms in the allotrope's homocyclic ring is 12.

BACKGROUND OF THE INVENTION

Cyclic sulfur allotropes and routes for their synthesis from sulfur-containing moieties have been described in the literature. For example, cyclododecasulfur, also referred to herein as $S_{12}$, is known to be present in thermally equilibrated sulfur allotrope mixtures in concentrations dependent on the equilibration temperature, ranging from about 0.39 wt % to 0.49 wt % between 116° C. and 387° C. (see Steudel, R.; Strauss, R.; Koch, L., "Quantitative HPLC Analysis and Thermodynamics of Sulfur Melts", Angew. Chem. Int. Ed. Engl., 24(1), 1985, pp. 59-60).

Steudel et al describe a method for $S_{12}$ synthesis in which cyclooctasulfur, also known as $S_8$, is heated to an equilibration temperature of 200° C., cooled to 140° C., and quenched in liquid nitrogen. $S_{12}$ is recovered from the solid allotrope mixture by multiple extractions, recrystallizations, decantations, and filtrations from very cold carbon disulfide with an overall yield on the sulfur fed of slightly over 0.21 percent. The melting point of the purified $S_{12}$ is reported as 146-148° C., the generally quoted melting point of purified $S_{12}$. (Steudel, R.; Mäusle, H-J., "Detection of Large-Ring Sulfur Molecules in Liquid Sulfur: Simple Preparation of $S_{12}$, $\alpha$-$S_{18}$, $S_{20}$ from $S_8$", Angew. Chem. Int. Ed. Engl., 18(2), 1979, pp. 152-53; and, Steudel, R.; Eckert, B., "Solid Sulfur Allotropes", Topics in Current Chemistry (2003) 230, pp. 1-79).

Schmidt and Block describe a method for the synthesis of $S_{12}$ in which sulfur is heated at 200° C. for 10 min and quenched in water. The resulting solids are stirred for 12 hours with a 6:1 mass ratio of $CS_2$ at room temperature, followed by filtration of insoluble polymeric sulfur, concentration of mother liquor, and recrystallization of crude $S_{12}$ from the remaining liquor at -30° C. The remaining $S_8$ is dissolved out of the $S_{12}$ solids with $CS_2$, and $S_{12}$ crystals are dried. The dried $S_{12}$, at a yield of 0.1% of the feed $S_8$, has a melting point of 140-142° C., with a higher melting point of 146-148° C. after recrystallization from benzene. (Schmidt, M.; Block, H.-D., "Occurrence of Cyclododecasulfur Compound in Sulfur Melts", Angew. Chem. Int. Ed. Engl., 6(11), 1967, pp. 955-56).

Mäusle and Steudel describe a cyclic sulfur allotrope synthesis method in which dichlorodisulfide dissolved in $CS_2$ reacts with aqueous solutions of potassium iodide to form unstable diiododisulfide and potassium chloride, which spontaneously decomposes into a mixture of even number homocyclic rings $S_6$, $S_8$, $S_{10}$, $S_{12}$, $S_{18}$, and larger, and 12. Typical yields are 36% $S_6$ and about 1 to 2% 812. (Mäusle, H. J.; Steudel, R., "Simple preparation of Cyclohexasulfur ($S_6$) from dichlorodisulfane ($S_2Cl_2$) and ionic iodides", Z. Anorg. Allg. Chem. 463, 1980, pp. 27-31).

Yet another approach to the synthesis of $S_{12}$ is described by Schmidt and Wilhelm (Schmidt, M.; Wilhelm, E., "Cyclododecasulfur, $S_{12}$", Angew. Chem. Int. Ed. Engl., 5(11), 1966, pp. 964-65). This method includes the metathesis of dichlorosulfides with polysulfanes, with corresponding generation of by-product HCl:

$$Cl_2S_x + H_2S_y \rightarrow 2HCl + S_{12} \text{ with } x+y=12$$

Schmidt and Wilhelm combine dropwise mixtures of $S_4Cl_2$ in $CS_2$ and $H_2S_8$ in $CS_2$ into a mixture of diethylether and $CS_2$ over 25 hours. After twelve hours, crude Sit crystals are filtered off periodically. The resultant crude $S_{12}$ is redissolved in $CS_2$ held at 40° C., and recrystallized by concentration of the crude $S_{12}$—$CS_2$ solution. Final recrystallization is from benzene, with an overall $S_{12}$ yield of 15% to 20% based on the sulfur fed.

Yet another method for cyclic sulfur allotrope synthesis involves the reaction of a sulfur transfer agent, bis($\pi$-cyclopentadienyl)-titanium(IV) pentasulfide, (titanocene pentasulfide) or $(C_5H_5)_2Ti(S_5)$ with sulfur dichloride ($SCl_2$) to form titanocene dichloride, $S_6$, and some $S_{12}$. In this method, $(C_5H_5)_2Ti(S_5)$ in $CS_2$ is treated with $SCl_2$ in $CS_2$ at 0° C. The filtrate containing $S_6$ and $S_{12}$ is filtered from the titanocene dichloride precipitate and evaporated to give an orange-yellow precipitate. $S_6$ is dissolved with cold $CS_2$ and the remaining solids are dissolved in hot $CS_2$. $S_{12}$ is recovered by cooling and crystallization from the final $CS_2$ solution. The overall sulfur yield is 87% to $S_6$ and 11% to $S_{12}$ (see Schmidt, M.; Block, B.; Block, H. D.; Köpf, H.; Wilhelm, E., "Cycloheptasulfur, $S_7$, and Cyclodecasulfur, $S_{10}$—Two New Sulfur Rings", Angew. Chem. Int. Ed. Engl., 7(8), 1968, pp. 632-33).

Prior art methods for manufacturing cyclic sulfur allotropes all suffer from one or more drawbacks such as low yields, multiple convoluted manufacturing steps, expensive, complex, and limited-availability starting materials and intermediates and tedious isolation and purification of end products. Most work in this field has accordingly been limited to academic endeavor, and commercially acceptable methods for cost-effective, efficient large-scale production have not heretofore been reported. A continuing need therefore exists for a robust, high-yield, safe, and cost-effective method for the manufacture of cyclic sulfur allotropes, and specifically cyclododecasulfur, that meets industrial criteria for commercial implementation.

SUMMARY OF THE INVENTION

The present invention relates to a method for the manufacture of a cyclic sulfur allotrope, and specifically cyclododecasulfur, wherein the number of sulfur (S) atoms in the allotrope's homocyclic ring is 12. The method includes reacting a metallasulfur derivative with an oxidizing agent in a reaction zone to form a cyclododecasulfur-containing reaction mixture that contains the cyclododecasulfur. The method preferably further includes isolating the cyclododecasulfur from the cyclododecasulfur—containing reaction mixture. The method of the present invention is particularly useful for the manufacture of cyclododecasulfur, described herein as a cyclic sulfur allotrope having 12 sulfur atoms in the homocyclic ring, that is useful in vulcanizing compositions for use in forming a vulcanized article, as disclosed and claimed in pending U.S. patent application Ser. No. 15/015,165 having common assignee herewith, the disclosure of which is incorporated herein by reference.

Further aspects and areas of applicability will become apparent from the description provided herein. It should be understood that the description and specific examples are intended for purposes of illustration only and are not intended to limit the spirit and scope of the present invention.

DETAILED DESCRIPTION

As utilized herein, the following terms or phrases are defined as follows:

"Cyclic Sulfur Allotrope" means a sulfur compound characterized by a homocyclic ring of sulfur atoms.

"Cyclododecasulfur" means a cyclic sulfur allotrope with twelve sulfur atoms in its homocyclic ring, also referred to herein as $S_{12}$.

"Metallasulfur derivative" means a compound containing divalent sulfur (S) atoms and metal (M) atoms with a ratio of sulfur to metal atoms of at least 2:1 (S:M≥2.0). The defining structural unit of such derivatives may be represented as:

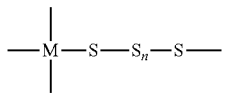

In which the metal atom (M) may be divalent or multivalent and the sulfur atoms (S) are divalent and form a chain with n≥0. The compound may be linear or branched, it may be cyclic, multicyclic, oligomeric or polymeric and it may contain other elements, ligands, cations or anions bonded or coordinated to the metal atom (inner- or outer-sphere), without limitation.

"Metallacylcosulfane" means a metallasulfur derivative with at least one cyclic structural feature containing sulfur and metal atoms, preferably only sulfur and metal atoms, with at least two sulfur atoms and one or more metal atoms.

"Sulfur templating agent" or "Sulfur templating agents" mean a compound, or combination of compounds and elements, which when reacted with elemental sulfur form a metallasulfur derivative.

"Oxidizing agent" means an agent which is (i) reduced by a metallasulfur derivative; (ii) promotes the release of the sulfur contained in the metallasulfur derivative and (iii) does not add sulfur from its composition to the cyclododecasulfur being produced in the process.

"Pseudohalogen" means a molecule or functional group with properties and a reactivity profile similar to a halogen (see e.g. Inorganic Chemistry by Duward Shriver, P. W. Atkins and Cooper Langford, W. H. Freeman & Co., 1990, pp 407-408).

The present invention is a method for manufacture of a cyclic sulfur allotrope, and specifically cyclododecasulfur, wherein the number of sulfur (S) atoms in the allotrope's homocyclic ring is 12. Similar methods may be used to form polymeric sulfur, and are claimed in a copending application filed herewith having common assignee.

The method of the present invention includes reacting a metallasulfur derivative with an oxidizing agent. A suitable metallasulfur derivative is characterized by the formula

wherein
L is a monodentate or polydentate ligand species which may be the same or different when x>1;
x is the total number of ligand species L and is from 0 to 6 inclusive;
M is a metal atom;
y is the total number of metal atoms and is from 1 to 4 inclusive;
S is a sulfur atom;
z is the number of sulfur atoms, and is from 1 to 12 inclusive;
u represents the charge of the metallasulfur derivative and may be from −6 to +6 inclusive;
v is the number of metallasulfur derivative units in an oligomeric or polymeric structure;
I is an ionic atom or group and may be cationic or anionic; and w is the number of cationic or anionic atoms or groups, as required to provide charge neutrality.

The ligand species may be mono- or polydentate and may be charged or neutral. Suitable ligand species are cyclopentadienyl or substituted cyclopentadienyl rings; amines such as primary, secondary, and tertiary alkyl or aryl linear or cyclic amines and may also be diamines or triamines or other polyamines such as ethylenediamine and ethylenetriamine and their derivatives, piperidine and derivatives, and pyrrolidine and derivatives; or heteroaromatic derivatives such as pyridine and pyridine derivatives or imidazole and imidazole derivatives. Preferred amines include but are not limited to tetraalkyl ethylenediamines, such as tetramethyl ethylenediamine (TMEDA), tetraethyl ethylenediamine, tetrapropyl ethylenediamine, tetrabutyl ethylenediamine; diethylene-triamine and derivatives such as pentamethyldiethylenetriamine (PMDETA); pyridine and derivatives of pyridine, such as bipyridine, 4-(N,N-dimethylaminopyridine (DMAP), picolines, lutidines, quinuclidines; imidazole and derivatives of imidazole such as N-methylimidazole, N-ethylimidazole, N-propylimidazole, and N-butylimidazole.

Suitable metals for the substituent M above include copper, zinc, iron, nickel, cobalt, molybdenum, manganese, chromium, titanium, zirconium, hafnium, cadmium, mercury; and precious and rare earth metals such as rhodium, platinum, palladium, gold, silver, and iridium. A preferred metal is zinc.

Particularly suitable metallasulfur derivatives for the method of the present invention are metallacyclosulfanes. Preferred metallacyclosulfanes include those depicted below as A, B, C and D. Other metallasulfur derivatives are oligomeric or polymeric species and may be linear as depicted in E below or branched as depicted in F below with the metal atoms serving as branch points.

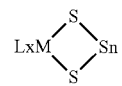

A

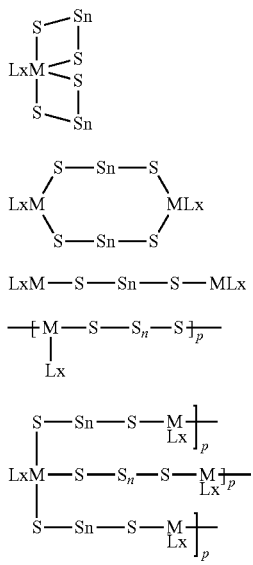

B

C

D

E

F

Metallasulfur derivatives may contain charged ligand species. For instance, a suitable metallasulfur derivative for the formation of a cyclododecasulfur compound is shown below:

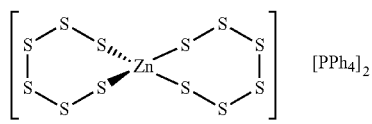

It contains only sulfur atoms bonded to zinc in two metallacyclosulfane rings and two tetraphenyl phosphonium ion groups to neutralize the dianionic charge of the metallasulfur derivative.

A related metallasulfur derivative which contains ligands is illustrated below:

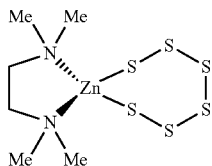

In this case a TMEDA ligand coordinated to zinc replaces a hexasulfide dianion, and thus the metallasulfur derivative is not anionic, it is neutral.

A particularly preferred class of metallacyclosulfanes for the method of the present invention are those containing an N-donor zinc complex. Even more particularly, when the intended cyclic sulfur allotrope is cyclododecasulfur, metallacyclosulfanes having four to six sulfur atoms and N-donor ligands coordinated to the zinc are preferred. Such complexes are formed by reacting elemental sulfur, also referred to herein as cyclooctasulfur or $S_8$, with metallic zinc in a solvent composed of, or containing, a donor amine, diamine or polyamine templating agent as described in more detail below. Examples of N-donor-zinc-cyclosulfanes include $(TMEDA)Zn(S_6)$, $(DMAP)_2Zn(S_6)$, $(pyridine)_2Zn(S_6)$, $(methylimidazole)_2Zn(S_6)$, $(quinuclidine)_2Zn(S_6)$, $(PMDETA)Zn(S_4)$, and $(bipyridine)_2Zn(S_6)$. The zinc complex, $(TMEDA)Zn(S_6)$, is a particularly preferred metallacyclosulfane in the method of the present invention and can be formed by reacting cyclooctasulfur, tetramethylethylenediamine and zinc. We have found that these metallacyclosulfane-forming reactions are best accomplished in the presence of water, as in Example 14 in which the addition of water consistently produced $(TMEDA)Zn(S_6)$ complex in high yields and purity even with low grade TMEDA.

U.S. Pat. No. 6,420,581, the disclosure of which is incorporated herein by reference in its entirety, relates to processes of producing zinc hexasulfide amine complexes that are suitable for use according to the present invention. These processes comprise reacting zinc, sulfur and a molar excess of amine at an elevated temperature to obtain a reaction mixture comprising zinc hexasulfide amine complexes and excess amine. A first solvent in which the zinc hexasulfide amine complexes are largely not soluble is added to obtain a slurry of the reaction mixture. The zinc hexasulfide amine complexes may be recovered in a subsequent separation process.

The metallasulfur derivatives of the method of the present invention may be formed by reacting elemental sulfur with a sulfur templating agent. Accordingly, in a preferred embodiment, the method of the present invention includes the step of reacting elemental sulfur with a sulfur templating agent to form a metallasulfur derivative prior to the step of reacting the metallasulfur derivative with an oxidizing agent.

Suitable sulfur templating agents for use in this embodiment of the method of the present invention include those characterized by the formula:

$$L_xM_y$$

wherein
L is a monodentate or polydentate ligand species which may be the same or different when x>1;
x is the total number of ligand species L and is from 1 to 6 inclusive;
M is a metal atom; and
y is the total number of metal atoms and is from 1 to 4 inclusive.

The ligand species may be mono- or polydentate. Suitable ligand species are cyclopentadienyl or substituted cyclopentadienyl rings; amines such as primary, secondary, and tertiary alkyl or aryl linear or cyclic amines and may also be diamines or triamines or other polyamines such as ethylenediamine and ethylenetriamine and their derivatives, piperidine and derivatives, and pyrrolidine and derivatives; or heteroaromatic derivatives such as pyridine and pyridine derivatives or imidazole and imidazole derivatives.

Preferred amines include but are not limited to tetraalkyl ethylenediamines, such as tetramethyl ethylenediamine (TMEDA), tetraethyl ethylenediamine, tetrapropyl ethylenediamine, tetrabutyl ethylenediamine; diethylene-triamine and derivatives such as pentamethyldiethylenetriamine (PMDETA); pyridine and derivatives of pyridine, such as bipyridine, 4-(N,N-dimethylaminopyridine (DMAP), picolines, lutidines, quinuclidines; imidazole and derivatives of imidazole such as N-methylimidazole, N-ethylimidazole, N-propylimidazole, and N-butylimidazole.

Suitable metals for the substituent M above include copper, zinc, iron, nickel, cobalt, molybdenum, manganese, chromium, titanium, zirconium, hafnium, cadmium, mercury; and precious and rare earth metals such as rhodium, platinum, palladium, gold, silver, and iridium. A preferred metal is zinc.

In the method of the present invention, the above-described metallasulfur derivative is reacted with an oxidizing agent. An appropriate oxidizing agent is any agent which is reduced by a metallasulfur derivative and promotes the release of the sulfur contained in the metallasulfur derivative. In addition, the oxidizing agent does not add sulfur from its composition to the cyclododecasulfur being produced in the process.

Non-limiting examples of such oxidizing agents include those of the formula:

X—X' wherein X and X' are the same or different and are selected from the group consisting of halogens and pseudohaolgens. Preferably, X and X' are either both chlorine or bromine and accordingly the oxidizing agent for the method of the present invention is either molecular bromine ($Br_2$) or molecular chlorine ($Cl_2$). X and X' may also be pseudohalogen groups such as cyanide, thiocyanide, sulfate, thiosulfate, sulfonate or thiosulfonate. In the embodiment where the pseudohalogen groups are cyanide or thiocyanide, the oxidizing agent X—X' would be dicyanogen or dithiocyanogen, respectively. In another embodiment wherein the pseudohalogen groups are sulfate, thiosulfate, sulfonate or thiosulfonate, it will be understood that the corresponding persulfate or perthiosulfate does not transfer sulfur atoms to the cyclododecasulfur being produced in the method of the present invention.

Another suitable oxidizing agent is molecular oxygen ($O_2$). When molecular oxygen is the oxidizing agent X and X' above are oxygen atoms. In the embodiment where the oxidizing agent is molecular oxygen, the molecular oxygen may, or may not, require the addition of a catalyst which promotes and/or accelerates the rate of electron transfer from the sulfur in the metallasulfur derivative to the oxidant, such that the oxidizing agent may include molecular oxygen and a catalyst. Such catalysts may be metals or metal complexes and examples of such complexes include the complexes of Fe(II), but other metals such as manganese, vanadium, molybdenum and copper are also common. Any substance which, in combination with molecular oxygen, will induce the desired oxidation of a metallasulfur derivative is within the scope of catalyst as described herein.

While the oxidizing agent for the method of the present invention has been described above in the context of suitable chemical compounds, it will be understood by a person of ordinary skill that, in general, electrochemically generated oxidants are capable of acting as oxidizing agents and may therefore be useful oxidizing agents in the method of the present invention. Examples include hydrogen peroxide, alkyl- and acyl peroxides, halogen atom radicals, and high oxidation state metal-centered oxidants such as Ce(IV) and Ir(V). Anodic oxidation of metallasulfur derivatives may include a catalyst at the anode to enable facile and selective oxidation. Such species may be used in combination with or in conjunction with molecular oxygen as the oxidizing agent for the method of the present invention.

Yet other suitable oxidizing agents include sulfuryl halides such as $SO_2Cl_2$ and $SO_2Br_2$ in which the $SO_2$ moiety is not incorporated into the cyclododecasulfur being produced by the method of the present invention.

In the method of the present invention, the stoichiometry of the oxidizing agent to the metallasulfur derivative may depend on the composition and structure of the metallasulfur derivative. In one embodiment of the method of the present invention, the stoichiometric ratio of the oxidizing agent to the metallasulfur derivative is selected so that one equivalent of oxidizing agent (X—X') is present for every two M-S bonds in the metallasulfur derivative. For the production of a cyclododecasulfur compound, if the metallasulfur derivative has one metal-sulfur bond for every three sulfur atoms then one equivalent of an oxidizing agent X—X' may be combined with a weight of metallasulfur derivative equal to six equivalents of sulfur. Examples of suitable ratios of oxidizing agent to metallasulfur derivative include: 1 mole of (TMEDA)Zn($S_6$) to 1 mole of $Br_2$; 1 mole of (TMEDA)Zn($S_6$) to 1 mole of $Cl_2$; 1 mole of $(C_5H_5)_2Ti(S_5)$ to 1 mole of $Cl_2$; 1 mole of $[PPh_4]_2[Zn(S_6)_2]$ to 2 moles of $Br_2$; 1 mole of $[PPh_4]_2[Zn(S_6)_2]$ to 2 moles of $Cl_2$; 1 mole of (N-methyl imidazole)$_2$Zn($S_6$) to 1 mole of $Br_2$; 1 mole of (N-methyl imidazole)$_2$Zn($S_6$) to 1 of mole $Cl_2$; 1 mole of (PMDETA)Zn($S_4$) to 1 mole of $Br_2$.

In another aspect of the method of the present invention, the stoichiometry of the oxidizing agent (X—X') to the metallasulfur derivative may be selected so as to increase the purity of the final cyclododecasulfur product. Thus, in a preferred embodiment, a substoichiometric (i.e. less than one equivalent) ratio of the oxidizing agent to the metallasulfur derivative is selected in order to synthesize a cyclododecasulfur mixture having lower levels of halogens. In this aspect, the stoichiometric ratio of the oxidizing agent to the metallasulfur derivative is selected so that less than one equivalent of the oxidizing agent is present for every two M-S bonds in the metallasulfur derivative. For the production of a cyclododecasulfur compound, if the metallasulfur derivative has one metal-sulfur bond for every three sulfur atoms then substoichiometric amounts of an oxidizing agent X—X' may be combined with a weight of metallasulfur derivative equal to six equivalents of sulfur. In this aspect, examples of suitable ratios of oxidizing agent to metallasulfur derivative include: 1 mole of (TMEDA)Zn($S_6$) to 0.90-0.99 mole of $Br_2$; 1 mole of (TMEDA)Zn($S_6$) to 0.90-0.99 mole of $Cl_2$; 1 mole of $(C_5H_5)_2Ti(S_5)$ to 0.90-0.99 mole of $Cl_2$; 1 mole of $[PPh_4]_2[Zn(S_6)_2]$ to 1.80-1.99 moles of $Br_2$; 1 mole of $[PPh_4]_2[Zn(S_6)_2]$ to 1.80-1.99 moles of $Cl_2$; 1 mole of (N-methyl imidazole)$_2$Zn($S_6$) to 0.90-0.99 mole of $Br_2$; 1 mole of (N-methyl imidazole)$_2$Zn($S_6$) to 0.90-0.99 mole $Cl_2$; 1 mole of (PMDETA)Zn($S_6$) to 0.90-0.99 mole of $Br_2$.

In one embodiment, the method of the present invention is a method for the manufacture of a cyclododecasulfur compound. In this embodiment, a preferred metallasulfur derivative is a tetramethylethylene-diamine/Zn($S_6$) complex. The tetramethylethylene-diamine/Zn($S_6$) complex is most preferably formed in situ by reacting tetramethylethylenediamine and zinc in the presence of elemental sulfur. Accordingly, in this embodiment, the templating agent is formed in situ in the presence of the elemental sulfur with which it reacts in the step for reacting the templating agent with the elemental sulfur.

According to the invention, cyclododecasulfur compound was formed in unexpectedly high yield by reacting one mole of the zinc-cyclohexasulfane (TMEDA)Zn($S_6$) with one mole of oxidizing agent $Br_2$ to form a theoretical ½ mole of cyclododecasulfur. Yields of cyclododecasulfur approaching 70% or more based on the atoms of sulfur contained in the initial reaction feed may be achieved. Such yields are more than five times those achieved by methods described in the prior art. In another aspect, a substoichiometric (i.e. less than one equivalent) ratio of the oxidizing agent to the metallasulfur derivative may be selected in order to synthesize a cyclododecasulfur mixture having lower levels of halogens.

The method of the present invention may be performed at a wide range of temperature, pressure, and concentration ranges. Suitable reaction temperatures are from −78° to 100° C., or between −45° C. and 100° C., more typically −10 to 40° C. In an embodiment wherein $(TMEDA)Zn(S_6)$ is selected as the metallacyclosulfane and $Br_2$ is selected as the sulfur-free oxidizing agent in the manufacture of cyclododecasulfur compound, typical reaction temperatures are from −78° C. to 60° C., or from −30° C. to 60° C., more preferably −10° C. to 40° C. In an embodiment wherein $[PPh_4]_2[Zn(S_6)_2]$ is selected as the metallacyclosulfane and either $Br_2$ or $Cl_2$ as the oxidizing agent, typical reaction temperatures are from −78° C. to 60° C., or from −30° C. to 60° C., more preferably −10° C. to 40° C.

The metallasulfur derivative in the reacting step may be in any physical form desirable to facilitate the reaction. Suitable forms include solid, slurry in an appropriate solvent, or solution in an appropriate solvent. Accordingly, in one embodiment of the method of the present invention, the method includes forming a slurry of the metallasulfur derivative in a solvent prior to the reacting step. In another embodiment of the method of the present invention, the method includes forming a solution of the metallasulfur derivative in a solvent prior to the reacting step. When a slurry or solution form is utilized, typical metallasulfur derivative concentrations for the slurry or solution are 0.5 to 30 weight percent, more typically 2 to 25 weight percent, based on the total weight of the slurry or solution. Suitable solvents useful for the slurry or solution form in the reacting step include halogenated solvents of one to 12 carbon atoms and one halogen atom up to perhalogenated content. Examples of halogenated solvents include methylene chloride, chloroform, carbon tetrachloride, carbon tetrabromide, methylene bromide, bromoform, bromobenzene, chlorobenzene, chlorotoluenes, dichlorobenzenes, dibromobenzenes. Other suitable solvents include alkanes of 5 to 20 carbons, aromatics, alkyl aromatics of 7 to 20 carbons. Examples are pentanes, hexanes, cyclohexane, heptanes, octanes, decanes, benzene, toluene, xylenes, mesitylene, ethyl benzene and the like. One or more combinations of solvents may also be utilized.

Similarly, the oxidizing agent in the reacting step may be in any physical form desirable to facilitate the reaction. Preferably, the oxidizing agent is in the form of a dispersion in a suitable dispersant. Accordingly, in one embodiment of the method of the present invention, the method includes forming a dispersion of the oxidizing agent in a dispersant prior to the reacting step. Typically, the oxidizing agent will be present in the dispersion in an amount of 0.5 to 60 wt % based on the total weight of the dispersion, more typically 1 to 25 wt % based on the total weight of the dispersion. Examples of dispersants include methylene chloride, chloroform, carbon tetrachloride, carbon tetrabromide, methylene bromide, bromoform, bromobenzene, chlorobenzene, chlorotoluenes, dichlorobenzenes, and dibromobenzenes.

In the method of the present invention, the step of reacting the metallasulfur derivative with the oxidizing agent is typically initiated and at least partially performed in a reaction zone. The reaction zone is generally defined as the volume or space wherein the step of reacting the metallasulfur derivative and the oxidizing agent commences and at least partially progresses toward completion. As the method of the present invention may be performed as a batch or semi-batch operation or continuous operation, and in any mode or reactor format known in the art including plug flow and stirred tank reactor constructions, the reaction zone may be configured according to factors such as for example capacity expectations; available manufacturing/plant area and capital; and utilities.

As the reaction of the reacting step is exothermic, the reacting step preferably includes removing heat of reaction from the reaction zone. In the embodiment wherein one or more of the metallasulfur derivative and the oxidizing agent are in a form that employs a solvent (slurry or solution for the metallsulfur derivative, or dispersant for the oxidizing agent), the heat removal step may include operating the step at a temperature and pressure to effect boiling of the solvent, solvents or dispersants. Alternatively, heat removal can be achieved by adding additional solvent or reactants into the reaction zone or by transferring heat from the reaction zone via a commercially available and well-known external heat exchange device such as a shell and tube or spiral wound heat exchanger.

The method of the present invention may be performed as a batch operation wherein reactants (metallasulfur derivative and oxidizing agent) are charged simultaneously or sequentially to the reaction zone. In one embodiment, wherein sequential addition of reactants is utilized, the reacting step of the method of the present invention may include first adding the oxidizing agent to the reaction zone then adding the metallasulfur derivative to the reaction zone. For sequential addition, the metallasulfur derivative may be in slurry or solution form and the oxidizing agent in dispersion form. In another embodiment, wherein simultaneous addition of reactants is utilized, the reacting step of the method of the present invention may include simultaneously adding the oxidizing agent and the metallasulfur derivative to the reaction zone.

Alternatively, the method of the present invention may be performed in plug-flow continuous mode, wherein reactants (metallasulfur derivative and oxidizing agent) are charged as separate continuous streams in such a manner to enhance mixing, such as impinging jets, into a static mixer, or a simple turbulent plug flow tubular reactor.

The reacting step of the present invention will typically extend for a period of from 30 seconds to 3 hours, preferably 1 minute to 2 hours and more preferably 2 minutes to 1 hour. When $(TMEDA)Zn(S_6)$ is utilized as the metallasulfur derivative and $Br_2$ is utilized as the oxidizing agent in the manufacture of cyclododecasulfur, the reacting step of the present invention will typically extend for a period of from 1 minute to 1 hour, or from 5 minutes to 20 minutes. When $[PPh_4]_2[Zn(S_6)_2]$ is utilized as metallasulfur derivative and $Cl_2$ or $Br_2$ is utilized as the oxidizing agent, the reacting step of the present invention will typically extend for a period of 1 minute to 1 hour, or from 1 minute to 10 minutes.

The reacting step in the method of the present invention yields an $S_{12}$-containing reaction mixture. The reaction mixture typically contains the cyclic sulfur allotrope as the desired product as well as one or more of solvents, dispersants, reaction byproducts, and unreacted reactants, generally referred to herein as "impurities", at least some of which may be insoluble in various solvents. Examples of byproducts and impurities include cyclooctasulfur and other allotropes of sulfur such as cyclohexasulfur, cycloheptasulfur, and higher cyclosulfur derivatives; polymeric sulfur, either in amorphorous or crystalline forms; unreacted oxidizing agent; metallasulfur derivative and its partially reacted derivatives or oligomers thereof; ligand, such as TMEDA; metals, such as zinc, from the metallasulfur derivative synthesis; oxidant-sulfur derivatives, for example structures of the form X—Sn—X where X is Cl or Br and n is greater or equal to 1; metal-containing compounds, such as $ZnBr_2$, $ZnCl_2$, $(TMEDA)ZnBr_2$, and $(TMEDA) ZnCl_2$; and any solvents used in the reaction or isolation steps.

Accordingly, the method of the present invention may further include processes for isolating $S_{12}$ from the $S_{12}$-containing reaction mixture. Suitable techniques, methods, and treatment steps for isolating the cyclododecasulfur from the cyclododecasulfur-containing mixture may vary widely depending on, for example, the choice of oxidizing agent, metallasulfur derivative, amount of unreacted reactants, the corresponding reaction efficiency, yield, and the degree and the type of impurities and by-products and the like. The isolation process for $S_{12}$ may thus comprise one or more of the following steps: dissolving, heating, drying, acid treating, solvent washing, crystallizing, and sedimentation. It is understood that the isolation process may involve more than one of the same type of step. For example, an isolation process may comprise solvent washing, followed by dissolving, crystallization, a different solvent washing step, and drying.

Dissolving steps may include treating the $S_{12}$-containing mixture with a solvent for $S_{12}$ to form a dissolution liquor, followed by separating the dissolution liquor from insoluble impurities. Examples of impurities which may be separated from the desired cyclododecasulfur in a dissolution step include polymeric sulfur and other cyclic sulfur allotropes that exhibit low solubility in the solvent compared to $S_{12}$, metallasulfur derivatives, metals, and metal-containing compounds. Separating the dissolution liquor from insoluble impurities may utilize separation techniques known in the art, such as filtration, centrifugation, or sedimentation. Typically, separating the dissolution liquor from insoluble impurities occurs at a temperature at or above that of the prior dissolution step to ensure that the dissolved cyclododecasulfur remains dissolved during the separation operation.

Solvents utilized in the dissolving step are preferably chosen from the group consisting of alkanes, halogenated hydrocarbons, aromatics, and carbon disulfide ($CS_2$). We note that the cyclododecasulfur obtained according to the methods of the present invention exhibits solubilities in various solvents that depend, in part, on the temperature, and that differ significantly from the solubility of cyclooctasulfur and polymeric sulfur. For example, depending on temperature, cyclooctasulfur is 30 to 200 times more soluble than cyclododecasulfur, and cyclododecasulfur is at least an order of magnitude more soluble than polymeric sulfur, in p-xylene, chlorobenzene, and $CS_2$ (see Example 21).

Preferred dissolving solvents include those selected from the group consisting of $CS_2$, $C_5$ and larger alkanes, halogenated hydrocarbons of one to 12 carbon atoms and one halogen atom up to perhalogenated content. Examples of halogenated solvents include methylene chloride, chloroform, carbon tetrachloride, carbon tetrabromide, methylene bromide, bromoform, bromobenzene, chlorobenzene, chlorotoluenes, dichlorobenzenes, o-, m-, p-dibromobenzenes. Examples of alkane and aromatic dissolving solvents include o-, m-, p-xylenes, toluene, benzene, ethyl benzene, o-, m-, p-diisopropylbenzene, naphthalene, methyl naphthalenes, hexane and isomers, heptane and isomers, cyclohexane, methylcyclohexane, and decane.

We note that cyclododecasulfur exhibits relatively low solubility in many solvents, so the dissolution step is typically performed at an elevated temperature to minimize solvent usage, typically above 20° C. up to about 140° C. The solubility varies considerably with the identity of the solvent, so the preferred temperature is dependent on the solvent chosen. For example, when using $CS_2$ as the solvent for the dissolving step, a preferred temperature range is 30 to 90° C., or from 40 to 85° C. When using alkanes, halogenated hydrocarbons or aromatics as the solvent for the dissolving step, a preferred temperature range is 75 to 140° C., or from 90 to 125° C. The weight ratio of dissolving solvent to cyclic sulfur allotrope to be dissolved is typically about 500/1 to 50/1, more typically 300/1 to 100/1.

We note that the most thermodynamically stable form of sulfur is cyclooctasulfur. Cyclosulfur allotropes (including $S_{12}$) and polymeric sulfur are known to equilibrate to cyclooctasulfur upon heating to high temperatures for undisclosed time periods. For example, at 141° C., the equilibrium composition of liquid sulfur is about 93 wt % cyclooctasulfur, with less than 0.5 wt % of any other individual $C_{10}$ to $C_{23}$ cyclosulfur allotrope (including 0.48 wt % $S_{12}$) and polymeric sulfur (see Steudel, R.; Strauss, R.; Koch, L., "Quantitative HPLC Analysis and Thermodynamics of Sulfur Melts", Angew. Chem. Int. Ed. Engl., 24(1), 1985, pp. 59-60). Surprisingly, we have discovered that this thermodynamic instability may be used to isolate certain cyclosulfur derivatives in a heating step. Thus, the thermal decomposition of the cyclododecasulfur obtained according to the methods of the present invention differs significantly from that of polymeric sulfur. For example, upon heating a mixture of polymeric sulfur and cyclododecasulfur in p-xylene at 115° C. for two hours, 100% of the polymeric sulfur was decomposed to cyclooctasulfur, whereas less than 3% of the cyclododecasulfur was converted to cyclooctasulfur (see Examples 22 and 23).

In the heating purification step of the present invention, the $S_{12}$-containing reaction mixture may be heated in the presence of a solvent to decompose and dissolve in the solvent at least some of the undesired impurities, including polymeric sulfur, present in the $S_{12}$-containing reaction mixture, producing a heating liquor and undissolved $S_{12}$. Preferably, $S_{12}$ is largely insoluble at the heating temperature, whereas cyclooctasulfur, the decomposition product of the undesirable cyclosulfur allotropes and polymer are soluble at the heating temperature.

This heating step may include a method to separate the heating liquor from the undissolved $S_{12}$. Separating the heating liquor from $S_{12}$ may utilize separation techniques known in the art, such as filtration, centrifugation, or sedimentation. Typically, separating the heating liquor from $S_{12}$ occurs at a temperature at or above that of the prior heating step to ensure that the impurities in the heating liquor remain dissolved during the separation operation. It is understood that $S_{12}$ may be recovered from the heating liquor by an additional crystallizing step in accordance with the present invention.

The time required for the heating step to achieve impurity decomposition is dependent on, for example, the solvent chosen and the temperature. Typically, the treatment may be accomplished effectively in 10 minutes to 4 hours, or from 15 minutes to 90 minutes.

The solvent utilized in this heating step is preferably chosen from the group consisting of alkanes, halogenated hydrocarbons, and aromatics. Preferred heating solvents are selected from the group consisting of $C_5$ and larger alkanes, halogenated hydrocarbons of one to 12 carbon atoms and one halogen atom up to perhalogenated content. Examples of halogenated solvents include methylene chloride, chloroform, carbon tetrachloride, carbon tetrabromide, methylene bromide, bromoform, bromobenzene, chlorobenzene, chlorotoluenes, dichlorobenzenes, o-, m-, p-dibromobenzenes. Examples of alkane and aromatic dissolving solvents are o-, m-, p-xylenes, toluene, benzene, ethyl benzene, o-, m-, p-diisopropylbenzene, naphthalene, methyl naphthalenes, hexane and isomers, heptane and isomers, cyclohexane, methylcyclohexane, and decane.

The heating step is operated typically from about 70° C. to about 145° C., or from 80° C. to 130° C. The pressure used in the heating step is adjusted such that the solvent remains largely a liquid at the chosen temperature, typically pressures of about 1 bara to 20 bara. Thus the pressure preferably exceeds the vapor pressure of the solvent at the chosen temperature. More preferably the pressure is 1 bara to about 10 bara.

The $S_{12}$-containing mixture may contain residual metal from preparation of the metallasulfur derivative, as well as metal-containing compounds such as the metallasulfur derivative itself, and any by-products of the reaction of the metallasulfur derivative with the oxidizing agent. This metal content may be removed by an acid treating step. In the acid treating step of the present invention, the $S_{12}$-containing reaction mixture is contacted with an acid-containing solution, wherein the acid is one or more mineral acids, such as for example hydrochloric, hydrobromic, sulfuric, and phosphoric acids. The acids are typically in dilute aqueous form, more typically 0.1 to 15 weight percent, or from 1 to 8 weight percent in water.

The acid treating step is operated typically from about 0° C. to about 80° C., or from about 10° C. to about 50° C. The time required for the acid treatment step may be accomplished effectively in 10 minutes to 4 hours, or from 15 minutes to 120 minutes.

Sulfur allotropes are quite hydrophobic, and particles of such substances tend to agglomerate in aqueous environments such as in the acid treatment step. To improve dispersion and enhance reactivity with the acid solution, a small amount of dispersing agent may be added in the contacting step, preferably added with the aqueous acid stream. Examples of suitable dispersing agents for the acid treatment step are water miscible organics such as acetone, methanol, acetonitrile, ethylene glycol. Typical concentrations of the dispersing agent are 0.1 to 15 weight percent, more typically 0.2 to 10 weight percent. Once the acid treating is completed, the acid-treated cyclosulfur allotrope is preferably washed with neutral water to remove any residual acid content.

Solvent washing of the $S_{12}$ compound may be used to remove impurities with high solubility in the wash solvent, to displace another solvent, or to remove relatively small amounts of impurities of lower solubility in the wash solvent. Said washing step is accomplished by contacting the $S_{12}$-containing reaction mixture with a washing solvent followed by separating the $S_{12}$ from the washed mixture using known techniques such as decantation, sedimentation, filtration, or centrifugation. The washing treatment typically does not completely dissolve the $S_{12}$, but rather removes impurities soluble in the washing solvent. Preferred washing solvents include those selected from the group consisting of $CS_2$, alkanes, halogenated hydrocarbons, $C_3$ to $C_5$ ketones, $C_1$ to $C_3$ alcohols, $C_2$ to $C_5$ ethers, and aromatic solvents. Examples are o-, m-, p-xylenes, toluene, benzene, ethyl benzene, o-, m-, p-diisopropylbenzene, naphthalene, methyl naphthalenes, hexane and isomers, heptane and isomers, cyclohexane, methylcyclohexane, decane, chlorobenzene, bromobenzene, o-, m-, p-dichlorobenzene, methylene chloride, o-, m-, p-dibromobenzene-methanol, ethanaol, isopropanol, n-propanol, diethyl ether, methyl tert-butyl ether, benzene, acetone, methyl ethyl ketone. The weight ratio of washing solvent to $S_{12}$-containing mixture is typically about 0.1/1 to 3/1, more typically 0.25/1 to 2/1.

During the crystallizing step, the amount of solvent present and the temperature used may be selected so that any dissolved cyclooctasulfur and other undesirable impurities remain dissolved while the $S_{12}$ largely crystallizes. When using $CS_2$ as the solvent, the crystallizing step preferably includes cooling the dissolution liquor to a temperature of from −30 to 25° C., more preferably from −10 to 10° C. When using alkanes, halogenated hydrocarbons or aromatics as the solvent for dissolution, the crystallizing step preferably includes cooling the dissolution liquor to a temperature of from 0 to 80° C., more preferably 10 to 60° C.

Particle size distribution of the $S_{12}$ crystals may be controlled to the desired range by selecting the appropriate temperature, concentration, and rate of cooling. Rapid cooling and near-saturation concentrations tend to lead to more nucleation and smaller, more narrow particle size distribution. Slow cooling, with or without seed crystals, tends to lead to larger particles and a broader distribution of crystal sizes.

Once the $S_{12}$ is dissolved in a solvent, for example by the dissolving or heat treating steps of the present invention, the $S_{12}$ may be isolated in high purity by crystallizing from the solvent. The step of crystallizing dissolved $S_{12}$ to form $S_{12}$ crystals and a crystallization mother liquor may be accomplished by any means known in the art, such as cooling crystallization, evaporative crystallization, anti-solvent crystallization, or combinations thereof. Seed crystals may also be added to promote particle size growth and reduce excessive nucleation if desired. Cooling crystallization is a particularly preferred means of carrying the crystallizing step.

A preferred method of cooling crystallization for the isolation of $S_{12}$ is cooling impinging jet crystallization, in which a hot $S_{12}$-laden dissolution liquor stream is brought into contact with an $S_{12}$-lean cool solvent stream (comprising either the same solvent as the dissolution liquor or a different solvent, or a mixture of solvents) at high velocities in a confined mixing region. The small volume of the mixing region and the high turbulence result in rapid cooling to a desired equilibrated mixing temperature, high nucleation rates, and uniform particle size distribution, an important characteristic of crystalline $S_{12}$ for vulcanization applications.

In one aspect, the particle size distribution of the crystalline $S_{12}$ produced by a crystallizing step has a Dv(50) of 10 to 80 microns, with a Dv(90) less than 120 microns and a Dv(10) greater than 5 microns; more preferably, the Dv(50) is 20 to 60 microns, with a Dv(90) less than 80 microns and a Dv(10) greater than 10 microns.

The weight ratio of $S_{12}$-lean cool solvent stream to hot $S_{12}$-laden dissolution liquor stream used for impinging jet crystallization may vary depending on the cool and hot stream inlet temperatures and the desired equilibrated mixing temperature, but is typically from about 10/1 to 0.5/1, more typically from 5/1 to 2/1.

When using alkanes, halogenated hydrocarbons, or aromatics as the cool or hot solvents for impinging jet crystallization, the preferred cool solvent temperature is 40° C. to −30° C., or 30° C. to −10° C.; a preferred hot solvent temperature is 75 to 140° C., or from 90 to 125° C.; and the preferred equilibrated mixing temperature is 5° C. to 60° C., or 10° C. to 45° C. When using $CS_2$ as the cool or hot solvents for impinging jet crystallization, the preferred cool solvent temperature is 15° C. to −30° C., or 10° C. to −15° C.; the preferred hot solvent temperature is 35 to 75° C., or from 40 to 65° C.; and the preferred equilibrated mixing temperature is −5° C. to 25° C., or 0° C. to 20° C.

The impinging jet crystallizer is preferably designed such that the linear velocities of the cool and hot streams are from 0.5 to 20 m/sec, from or 1 to 10 m/sec, and maintain turbulent flow in the hot stream, cold stream, and mixture stream.

Surprisingly, it has been discovered that differences in the density of impurities in the $S_{12}$-containing mixture and the $S_{12}$ itself may be used to effect a purification of the $S_{12}$. In particular, $S_{12}$ may be separated from metal particles, for example zinc particles. Thus, in a sedimentation step, an $S_{12}$-containing mixture is contacted and mixed with a sedimentation solvent, causing suspension of particles within the sedimentation solvent resulting in a suspended slurry mixture. The suspended slurry mixture is then subjected to an external field of acceleration to effect a separation of types of particles into a settled particle layer and a suspended particle mixture. The external field of acceleration may be gravitational, centrifugal, magnetic, or electrostatic in nature.

For example, in the embodiment of the present invention wherein a crude $S_{12}$-containing mixture is produced from $Br_2$ oxidant and $(TMEDA)Zn(S_6)$ metallasulfur derivative, the $S_{12}$-containing mixture may be subjected to a sedimentation step with chlorobenzene as the sedimentation solvent, forming a suspended slurry mixture. Agitation of the suspended slurry mixture is ceased, and the suspended slurry mixture is subjected to simple gravity sedimentation, resulting in a settled particle layer comprising $S_{12}$ and large zinc particles, and a suspended particle mixture comprising mostly smaller zinc particles and sedimentation solvent. Decantation of the suspended particle mixture away from the selected particle layer results in reduction of the zinc content of the settled particle layer and enhancement of $S_{12}$ content.

The sedimentation step may be operated in batch or continuous mode and may be repeated one or more times to enhance the separation. Preferred temperatures for the sedimentation step are between 0 and 80° C., more preferably 20 to 45° C.

The sedimentation solvent may comprise a liquid compound, dissolved cyclooctasulfur, or other soluble impurities from the crude $S_{12}$-containing mixture. Preferably the sedimentation solvent has a density greater than 1 g/cc and less than about 1.8 g/cc at the sedimentation step temperature. Examples of useful liquid compounds for use as a component of the sedimentation solvent are $CS_2$ and halogenated hydrocarbons of one to 12 carbon atoms and one halogen atom up to perhalogenated content. Examples of halogenated solvents include methylene chloride, chloroform, carbon tetrachloride, carbon tetrabromide, methylene bromide, bromoform, bromobenzene, chlorobenzene, chlorotoluenes, dichlorobenzenes, o-, m-, p-dibromobenzenes. The presence of dissolved cyclooctasulfur in the sedimentation solvent increases the density of the sedimentation solvent and is favored, in particular when suspending smaller metal particles. The preferred amount of dissolved cyclooctasulfur is dependent on the liquid compound used and sedimentation temperature, but typically is from about 1 wt % to about 20 wt %.

As the products of other steps of the isolation process, such as dissolving, heat treating, acid treating, solvent washing, crystallizing, and sedimentation, result in solvent-wet cyclododecasulfur crystals, the isolating process may optionally include a step of drying the solvent-wet cyclododecasulfur crystals to form dried sulfur allotrope crystals. Drying of the solvent-wet cyclododecasulfur crystals may be accomplished by means known in the art, such as by inert gas sweep, heating, placing under vacuum, or combinations thereof. Typically, the drying step is accomplished at temperatures below the melting point of the cyclic sulfur allotrope, more typically from about 40° C. to about 110° C. at a pressure of less than 2 bara (bar absolute), typically at atmospheric pressure or down to about 0.05 bara.

A preferred isolating process for the method of the present invention includes (i) dissolving the $S_{12}$ from the $S_{12}$-containing reaction mixture by treating the $S_{12}$-containing mixture with a solvent for the $S_{12}$ to form a dissolution liquor, followed by separating insoluble impurities from the dissolution liquor; (ii) crystallizing the $S_{12}$ from the dissolution liquor to form $S_{12}$ crystals in a crystallization mother liquor, followed by separating the $S_{12}$ crystals from the crystallization mother liquor; and (iii) drying of the mother-liquor-wet $S_{12}$ crystals from the crystallizing step to produce a purified $S_{12}$ solid product.

In a second preferred embodiment, the isolating process includes (i) heating the $S_{12}$-containing reaction mixture in the presence of a solvent to decompose and dissolve in the heating solvent at least some of the impurities present in the $S_{12}$-containing reaction mixture and separating the remaining solids comprising the majority of the $S_{12}$ from a heating liquor. Further steps in this embodiment preferably include one or more of: (ii) contacting the solids separated in step (i) with acid; (iii) washing the acid from the solids-containing product of step (ii) with a water washing solvent; (iv) washing the water-washed, solids-containing product of step (iii) with a low boiling solvent; and (v) drying the washed solids to produce a purified $S_{12}$ solid product.

In a third preferred embodiment, the isolating process includes (i) heating the $S_{12}$-containing reaction mixture in the presence of a solvent to decompose and dissolve in the heating solvent at least some of the impurities present in the $S_{12}$-containing reaction mixture, and separating the remaining solids comprising the majority of the $S_{12}$ from a heating liquor. Further steps in this embodiment preferably include one or more of: (ii) contacting the solids separated in step (i) with a dissolving solvent to produce a dissolution liquor and insoluble impurities; (iii) crystallizing $S_{12}$ from the dissolution liquor of step (ii) to produce $S_{12}$ crystals and a crystallization mother liquor; and (iv) drying the solvent-wet crystallized solids to produce a purified $S_{12}$ solid product.

In a fourth preferred embodiment, the isolating process includes (i) heating the $S_{12}$-containing reaction mixture in the presence of a solvent to decompose and dissolve in the heating solvent at least some of the impurities present in the $S_{12}$-containing reaction mixture, and separating the remaining solids comprising the majority of the $S_{12}$ from a heating liquor. Further steps in this embodiment preferably include one or more of: (ii) contacting the solids separated in step (i) with a sedimentation solvent to produce a suspended slurry mixture and a settled particle layer; (iii) contacting the solids of the settled particle layer separated in step (ii) with a dissolving solvent to produce a dissolution liquor and insoluble impurities; (iv) crystallizing $S_{12}$ from the dissolution liquor of step (iii) to produce $S_{12}$ crystals and a crystallization mother liquor; and (v) drying the solvent-wet crystallized solids to produce a purified $S_{12}$ solid product.

The following examples, while provided to illustrate with specificity and detail the many aspects and advantages of the present invention, are not be interpreted as in any way limiting its scope. Variations, modifications and adaptations which do depart from the spirit of the present invention will be readily appreciated by one of ordinary skill in the art.

Analytical Methods

Differential Scanning Calorimetry (DSC)—

The differential scanning calorimetry method (DSC) to measure the melting point range of the cyclic sulfur allotrope compound involves a first heating scan, from which are determined the melting peak temperature(Tm1) and the exothermic peak temperature (Tex1). The instrument used was a TA's Q2000 DSC (RCS) with a refrigerated cooling system. The procedure used is described herein as follows.

The instrument was calibrated according to the manufacturers "User's Manual"; by setting the onset of the melting point of adamantane, indium and lead at −65.54° C., 156.60° C., and 327.47° C., respectively, and heat of fusion of Indium at 6.8 cal/g. A calibration specimen of about 3.0 mg was then scanned at a rate of 20° C./min. in the presence of helium with a flow rate of 50 cc/min. For sulfur-containing specimens, a similar method was used. A TA's Tzero aluminum pan and lid along with two aluminum hermetic lids were tared on a balance. About 3.0 mg of the sulfur-containing specimen was weighed into the Tzero pan, covered with the tared lid, and crimped using a TA's sample crimper with a pair of "Black" dies. The crimped specimen from the "Black" die stand was moved to the "Blue" die stand, where two tared hermetic lids were placed on the top of the specimen pan and crimped with the top "Blue" die. An empty crimped Tzero aluminum pan and lid along with 2 hermetic lids was prepared in a similar fashion as reference. The specimen and reference pans were placed in the DSC tray and cell at room temperature. After the DSC was cooled to −5° C. using a refrigerated cooling system, the specimen was heated from −5 to 200° C. at a rate of 20° C./min in the presence of helium. "Melt point onset" was defined as the temperature at the start of the endothermic melting event. Data analysis was performed using TA's software, Universal V4.7A, wherein, Tm1 refers to the low melting peak temperature occurring on the melting curve, using analysis option, "Signal Maximum". Tex1 refers to the exothermic peak temperature occurring right after Tm1, using analysis option, "Signal Maximum".

UniQuant (UQ)—

Samples were also analyzed using X-ray fluorescence and the UniQuant software package. UniQuant (UQ) is an x-ray fluorescence (XRF) analysis tool that affords standardless XRF analysis of samples. Samples can then be semi-quantitatively analyzed for up to 72 elements beginning with row three in the periodic table (i.e. Na to higher Z). The data are mathematically corrected for matrix differences between calibration standards and samples as well as absorption and enhancement effects; i.e. inter-element effects. Some factors that can affect the quality of results include granularity in the sample (leading to shadow effects), mineralogical effects (due to sample inhomogeneity), insufficient sample size, and lack of knowledge of the sample matrix. In cases where a sample was amenable to both, the XRF UQ analysis and the ICP-OES (i.e. quantitative) analysis generally agree within +/−10%. Samples were analyzed for Zn, Br, Cl, and S content by UQ.

ICP—

Approximately 100 milligrams of sample was weighed into a precleaned Quartz sample tube. Then 3 mL of concentrated nitric acid was added to each tube (Trace metal grade Fisher Chemical). Samples were microwave-digested using an Ultrawave Single Reaction Chamber Digestion System. After addition of scandium as an internal standard element (1 ppm level after final dilution), digested samples were diluted to a volume of 25 mL, yielding a final acid concentration of ~10% HNO3 (based on nitric acid added and expected consumption of nitric acid during the digestion). A 1 ppm scandium internal standard was added to each sample. A Perkin Elmer Optima 2100 ICP-OES instrument (PerkinElmer Inc., Waltham Mass.) was calibrated with a matrix matched 1 ppm calibration standard and blank. Each sample, including a method blank was then analyzed for Zn, S, Br, and Cl content.

X-Ray Diffraction (XRD)—Measurements were made on powder samples using a PANalytical Empyrean X-Ray Diffractometer (XRD) (Available from PANalytical Incorporated). The XRD utilized a Copper anode X-Ray Source operated at 45 kV and 40 mA. The system was configured for measurements in the Bragg Brentano θ/2θ reflection geometry. Diffraction measurements were collected from 5 to 80 degrees 2θ angle. The powder diffraction patterns for crystalline sulfur allotropes were identified by comparison to patterns from a purchased database (International Centre for Diffraction Data ICDD, Newtown Square, Pa., USA or equivalent) or to patterns of known reference standards. Quantitation of crystalline sulfur allotropes was performed by external calibration or the use of Reference Intensity Ratio (RIR) methodology.

Raman Spectroscopy—

The samples' Raman spectrum was measured using a Renishaw inVia confocal Raman microscope and WiRE 4.1 software with a 785 nm excitation laser and a 5× magnification microscope objective.

NMR—

Weigh approximately 0.0200 g of sample into a vial. Weigh approximately 0.0200 g of the internal standard, 1,4-dimethoxybenzene, into the same vial. Add approximately 1 mL of pyridine-d5, or other deuterated solvent that the material is soluble in. Take a $^1H$ NMR of the material and integrate the peak at δ 3.68 (6 protons). Integrate the two peaks at δ 2.45 and δ 2.25 (16 protons). Calculate the % purity using the following equation.

% Purity=100[(mg IS/MW IS)*(ʃsample/ʃIS)*(6/16)* (MW sample/mg sample)]

IS=internal standard
MW=molecular weight
f=value of the integration from the $^1H$ NMR Particle Size Distribution—

The particle size distribution of cycoldodecasulfur materials was measured by a laser light scattering technique using a Malvern Mastersizer 3000 instrument, capable of measuring a particle size range from 0.1-1000 μm, equipped with optics comprising; a max. 4 mW He—Ne, 632.8 nm red light source; nominal 10 mW LED, 470 nm blue light source; reverse Fourier (convergent beam) lens arrangement, effective focal length of 300 mm; with the detector in a log-spaced array arrangement, angular range of 0.015-144 degrees, and automatic alignment, The disperant (isopropanol) was added to the instrument and a small amount of cyclododecasulfur sample was added to the isopropanol to achieve a laser obscuration near 5%. The sample was mixed for 30 seconds to 60 seconds, and subjected to light scattering analysis, with the particle size distribution based on a Mie scattering model, using a refractive index of 1.93. The method reports volume-weighted diameters, with the following distribution terms defined as:

D[4,3] is the "volume-weighted mean", or "average" diameter, defined as:

$$D[4,3] = \frac{\sum f_i * d_i^4}{\sum f_i * d_i^3}$$

where fi is the fraction of the particle having a diameter of di.

Dv (10)—10% of the population lies below this size
Dv (50)—The volume "median diameter". 50% of the distribution above this value and 50% below
Dv (90)—90% of the distribution lies below the size Liquid Chromatrography—

The liquid chromatography (LC) method separates elemental sulfur species including $S_8$ and $S_{12}$. The sulfur species were identified by retention time determined from known samples. The quantity of $S_8$ was determined by comparing the peak area of $S_8$ in the unknown sample with that of $S_8$ standard solutions of known concentrations made in toluene. The following operating parameters apply to all LC analyses:

HPLC instrument: Agilent 1200 with quaternary pump and diode array detector
    Columns: Agilent, particle: Eclipse Plus $C_{18}$, particle size: 3.5 urn
    Pre-column filter: Upchurch 0.5 urn stainless steel frit, part no.: A316
    Guard column: Phenomenex "security guard" HPLC guard cartridge system with $C_{18}$ cartridge, part no.: KJO-4282
    Autosampler vials: from VWR, catalog number 500 779
    Flow rate: 0.8 mL/min
    Run time: 40 min
    Solvent: HPLC grade methanol isocratic
    Column temperature: 6° C.
    Detection wavelength: 254 nm, band width 16 nm Injection volume: 5 uL.

EXAMPLES

Preparation of a Cyclododecasulfur Compound from (TMEDA)Zn($S_6$)

Example 1.

Preparation of metallasulfur derivative (TMEDA)Zn($S_6$). Tetramethyl-ethylenediamine (TMEDA), (408 grams) and methanol (72 grams) were added to a 3 L, 3-neck glass flask equipped with a mechanical stirrer (reaching closely to the vessel walls), thermocouple, $N_2$ bubbler, water condenser, and electrical heating mantle. The system was purged with nitrogen and the temperature of the mixture adjusted to 35° C. Freshly ground cyclooctasulfur (powder) was added over five minutes while maintaining stirring at 425-450 rpm. The temperature was increased to 45° C. such that the freshly ground cyclooctasulfur was dissolved and whereupon 40 grams of metallic zinc powder (<10 micron particle size, >98% purity) was added over five minutes while maintaining stirring at 425-450 rpm. The gray-greenish yellow reactor contents were then heated slowly to 86° C. and agitated for 4 hours, or until yellow. Once yellow, the mixture was held for an additional two hours at temperature, with agitation. At the end of the reaction time, the flask was cooled to room temperature, the agitator turned off, and free liquid removed by vacuum extraction. Methanol (600 ml) was added to the flask to create a slurry, and agitated for one hour. The resulting slurry was then filtered on a vacuum Buchner filter (1 micron paper) and washed with two portions of 200 ml each of methanol. The solids were removed from the filter and dried overnight in a vacuum oven set at 50° C. and 0.1 MPa. Yield was near quantitative, with 233 grams of metallasulfur derivative (TMEDA)Zn($S_6$) complex, recovered at 97% purity as measured by NMR. Similar yields were uniformly achieved in multiple runs by carefully controlling mixing conditions.

Preparation of a Cyclododecasufur Compound ($S_{12}$).

Methylene chloride (750 mL) was added to a 2 L, 4-neck glass flask equipped with a mechanical stirrer, thermocouple, $N_2$ bubbler and stopper. Bromine (16.7 g, 104.5 mmol, 1.0 eq) as oxidizing agent was weighed into a bottle containing 50 mL $CH_2Cl_2$ and this mixture was added to the flask. The solution was cooled to 4° C. The zinc complex, (TMEDA)Zn($S_6$), from Example 1, (97.5% pure) (40 g, 104.3 mmol, 1.0 eq), was added all at once and washed in with 50 mL $CH_2Cl_2$. There was an immediate exotherm to 11° C. The solution was stirred for 15 minutes, filtered, washed with cold $CH_2Cl_2$ and suctioned dry. The solids were slurried in THF (250 mL), filtered and suctioned dry. The resultant solids were slurried in cold $CS_2$ (150 mL), filtered and suctioned dry to afford 10.2 g of a pale yellow solid (yield 50.8% based on sulfur in the zinc complex). Evaluation using the UQ elemental analysis method showed the material to be 96.6% sulfur (cyclododecasulfur compound ($S_{12}$) plus sulfur polymer by Raman spectroscopy), 2.67% zinc and 0.7% bromine.

The cyclododecasulfur compound was further isolated in a two-vessel system comprising an upper 2 L, jacketed 3-neck glass flask equipped with a mechanical stirrer, fine glass fritted filter plate, thermocouple, $N_2$ bubbler, dry ice trap, and bottom valve; and a lower 2 L, jacketed 3-neck glass flask equipped with a mechanical stirrer, water-cooled condenser and 1 L glass receiver pot, thermocouple, $N_2$ bubbler, dry ice trap, and bottom valve. To initiate the purification procedure, carbon disulfide (1200 grams) was added to the upper vessel along with the cyclododecasulfur compound from the above reaction step (10.2 g). The contents of the flask were heated to 40-42° C. with stirring. After agitation of the mixture for half of an hour, the bottom valve of the vessel was opened, and the free liquid pulled through the fritted glass filter into the lower flask. About half of the initial solids remained on the filter. The solution in the second vessel was cooled to −6° C. over a period of 20 minutes or less. During the cooling phase, fine light yellow crystalline cyclododecasulfur compound formed. The solution was stirred for about 15 minutes at a final temperature of −6° C., whereupon the bottom valve of the vessel was opened and the slurry of $S_{12}$—$CS_2$ was dropped onto a Buchner funnel fitted with 2 micron filter paper. The light yellow crystalline cyclododecasulfur compound was suctioned dry and scraped from the filter paper. The mother liquor from the final filtration was returned to the upper vessel, (containing residual solids), along with makeup $CS_2$ to give 1200 grams of liquid. The upper vessel was agitated and heated again to 40-42° C. and the filtering-cooling procedure was repeated to recover a second crop of purified cyclododecasulfur compound ($S_{12}$) crystals. After the final heating-dissolution step, about 0.26 grams of greenish-yellow solids remained on the upper fritted filter. The combined wet $S_{12}$ crystals were placed in a vacuum oven overnight at 30° C. and about 0.01 MPa to remove residual $CS_2$, to give 9.3 grams of dried, purified cyclododecasulfur compound. Evaluation by the UQ elemental method showed the material to be at least 99.9% sulfur (all $S_{12}$ by Raman), and less than 100 ppm of zinc and bromine. The melting point was determined first by DSC (20° C./min heating rate) and then using a thermal resistance melting point apparatus to be 162° C. and 157° C. respectively. Overall yield of sulfur to $S_{12}$ was 46%.

In examples 2 through 5, cyclododecasulfur compound was manufactured using the method of the present invention utilizing a single batch of (TMEDA)Zn($S_6$) as the metallasulfur derivative, bromine as the oxidizing agent and a variety of dispersants and solvents.

Example 2

Methylene chloride as solvent for metallasulfur derivative and dispersant for the oxidizing agent. To a 2 L round bottom flask equipped with a stir bar, nitrogen purge and cold water condenser, was added 900 mL of methylene chloride. The flask was cooled in an ice bath. About 25 mL of methylene chloride was added to a separate glass bottle and 18.29 g of bromine weighed into the same bottle and this combination was added to the round bottom flask and washed down with 25 mL of methylene chloride. Then 45.17 grams of (TMEDA)Zn($S_6$) complex, (94% purity by NMR, prepared according to the method of Example 1) was added to the flask and washed down with 50 mL of methylene chloride. The reaction was stirred for 15 minutes and then filtered using a Buchner funnel and 1 micron filter paper. The solids were then transferred to a second round bottom flask and slurried with 400 mL of THF. This slurry was stirred for 30 minutes and then filtered using a Buchner funnel and 1 micron filter paper. The resulting solids were then transferred to yet another round bottom flask and cooled in an ice bath. 150 mL of ice-cooled $CS_2$ was added to the third round bottom flask and stirred for 30 minutes. The mixture was then filtered using a Buchner funnel and 1 micron filter paper. The resulting solids on the filter paper were vacuum dried to afford 11.42 g of a pale yellow crystal material (yield of 50.0% based on sulfur in the zinc complex). Evaluation using the UQ elemental analysis method showed the material to be 93.25% sulfur (highly concentrated in cyclododecasulfur compound ($S_{12}$) with traces of cyclooctasulfur and sulfur polymer by Raman spectroscopy), 6.37% zinc and 0.38% bromine.

Example 3

Chlorobenzene as solvent for metallasulfur derivative and dispersant for oxidizing agent. To a 1 L round bottom flask equipped with a stir bar, nitrogen purge and cold water condenser, was added 400 mL of chlorobenzene. The flask was cooled in an ice bath. About 25 mL of chlorobenzene was added to a separate glass bottle and 8.06 grams of bromine weighed into the same bottle. This was added to the round bottom flask and washed down with 25 mL of chlorobenzene. Then 20 grams of (TMEDA)Zn($S_6$) complex, (94% purity by NMR, from the same batch as Example 1) was added to the flask and washed down with 50 mL of chlorobenzene. The reaction was stirred for 15 minutes and then filtered using a Buchner funnel and 1 micron filter paper. The solids were then transferred to a second round bottom flask and slurried with 200 mL of THF. This slurry was stirred for 30 minutes and then filtered using a Buchner funnel and 1 micron filter paper. The resulting solids were then transferred to yet another round bottom flask and cooled in an ice bath. 75 mL of ice-cooled $CS_2$ was added to the third round bottom flask and stirred for 30 minutes. The mixture was then filtered using a Buchner funnel and 1 micron filter paper. The resulting solids on the filter paper were vacuum dried to afford 7.29 g of a pale yellow crystal material (yield of 72% based on sulfur in the zinc complex). Evaluation using the UQ elemental analysis method showed the material to be 95.58% sulfur (highly concentrated in cyclododecasulfur compound ($S_{12}$) with traces of cyclooctasulfur and sulfur polymer by Raman spectroscopy), 4.34% zinc and 0.08% bromine.

Example 4 p-Xylene as solvent for metallasulfur derivative and dispersant for oxidizing agent. To a 1 L round bottom flask equipped with a stir bar, nitrogen purge and cold water condenser, was added 450 mL of p-xylene. The flask was cooled in an ice bath. Then 20 grams of (TMEDA)Zn($S_6$) complex, (94% purity by NMR, from the same batch as Example 1). 8.06 grams of bromine were weighed into a small vial and transferred to an addition funnel. Bromine was added slowly to the round bottom flask over 15 minutes. After bromine addition, the reaction was stirred for an additional 15 minutes and then filtered using a Buchner funnel and 1 micron filter paper. The solids were then transferred to a second round bottom flask and slurried with 200 mL of THF. This slurry was stirred for 30 minutes and then filtered using a Buchner funnel and 1 micron filter paper. The resulting solids were then transferred to yet another round bottom flask and cooled in an ice bath. 75 mL of ice-cooled $CS_2$ was added to the third round bottom flask and stirred for 30 minutes. The mixture was then filtered using a Buchner funnel and 1 micron filter paper. The resulting solids on the filter paper were vacuum dried to afford 6.85 g of a pale yellow crystal material (yield of 64.4% based on sulfur in the zinc complex). Evaluation using the UQ elemental analysis method showed the material to be 92.37% sulfur (highly concentrated in cyclododecasulfur compound ($S_{12}$) with traces of cyclooctasulfur and sulfur polymer by Raman spectroscopy), 6.85% zinc and 0.78% bromine.

Example 5

Methylene chloride as solvent for metallasulfur derivative and dispersant for oxidizing agent at reaction zone temperature of 15° C. Four liters of methylene chloride was added with stirring to a 12 liter jacketed cylindrical flask, fitted with a mechanical agitator, funnel, cooling water condenser, nitrogen bubbler, and cooling bath. Bromine, 100 grams, was added through the funnel and rinsed in with about 100 mL of methylene chloride. The contents of the flask were cooled to 15° C. Then 233.93 grams of (TMEDA)Zn($S_6$) complex, (99% purity by NMR, prepared in a fashion as in Example 1) was added to the reactor via the funnel and washed down with about 100 mL of methylene chloride. The reactor contents were stirred for 15 minutes and filtered using a Buchner funnel with 1 micron filter paper. About 3 L of THF was added to the flask and stirred for 30 minutes. The THF-washed solids were filtered using a Buchner funnel and 1 micron filter paper. The resulting THF-wet solids were further washed on a Buchner funnel with 100 mL of $CS_2$. The resulting solids on the filter paper were vacuum dried to afford 72.5 grams of a pale yellow crystal material (yield of 62% based on sulfur in the zinc complex). Evaluation using the UQ elemental analysis method showed the material to be 97.9% sulfur (highly concentrated in cyclododecasulfur compound ($S_{12}$) with traces of cyclooctasulfur and sulfur polymer by Raman spectroscopy), 1.72% zinc and 0.37% bromine.

Preparation of Cyclododecasulfur from (N-Methylimidazole)$_2$Zn($S_6$)

Example 6

Preparation of (N-methylimidazole)$_2$Zn($S_6$). Zinc (7.06 g, 108 mmol, 1.0 eq) and sulfur (20.86 g, 650 mmol, 6.02 eq) were stirred for 16 hours in dry N-methylimidazole (155 mL) under $N_2$. The dark red solution was cooled to room temperature, diluted with 200 mL of ethyl ether and held at 0° C. for 6 hours. The resulting solids were collected by filtration and recrystallized from N-methylimidazole and ethyl ether to afford 18.5 g of a bright yellow solid (40.3% yield). ICP showed 48.2% sulfur, 16.5% zinc, leaving 35.3% organic (calculated: 45.3% sulfur, 15.4% zinc, 38.7% organic). Quantitative NMR showed the material to be 97% pure.

Preparation of Cyclododecasulfur.

Bromine (6.03 g, 240 mmol, 1.0 eq) was added to 300 mL dichloromethane in a round bottom flask. The mixture was cooled to 1° C. (N-methylimidazole)$_2$Zn(S$_6$) was added all at once and washed in with 60 mL dichloromethane. An exotherm to 7° C. was observed. The orange color dissipated after 10 minutes of stirring at which point the temperature started to drop again. The solids were collected by filtration. The material was slurried in THF, collected by filtration and slurried in CS$_2$. The solids were collected by filtration and suction dried to afford 2.25 g of a pale yellow powder (31% yield). Raman showed the material to be mostly cyclododecasulfur compound with some cyclooctasulfur. ICP showed the material to be 88.9% sulfur, 7.7% zinc and 4.4% bromine.

Example 7

Preparation of [PPh$_4$]$_2$[Zn(S$_6$)$_2$]. Sodium sulfide nanohydrate (6.4 g, 26.7 mmol, 1.0 eq) and 160 mL water were added to a round bottom flask under nitrogen and purged well. Ground sulfur (2.33 g, 72.7 mmol, 2.72 eq) was added and the mixture was heated to 50° C. for 30 minutes (slurry). Tetraphenylphosphonium chloride and 270 mL water were added to a separate round bottom flask under nitrogen, purged well and heated to 50° C. for 30 minutes (almost all in solution). The tetraphenylphosphonium chloride solution was added to the first flask. There was the immediate appearance of bright orange crystals. The new mixture was stirred at 50° C. for 2 hours. The solids were collected by filtration and washed well with water. The crystals were re-slurried in 400 mL water and stirred for 2 hours. The solids were again captured by filtration and suction dried to afford 13.13 g of [PPh$_4$]$_2$[S$_6$] (100% yield based on sulfur).

Acetonitrile (100 mL) was added to a round bottom flask under nitrogen and purged well. [PPh$_4$]$_2$[S$_6$] (10 g, 11.5 mmol, 1.0 eq) and (TMEDA)Zn(S$_6$) (4.3 g, 11.5 mmol, 1.0 eq-99% purity by NMR) were added and washed in with 50 mL acetonitrile. The solution turned dark blue when the phosphorus compound was added and bright yellow when the (TMEDA)Zn(S$_6$) compound was added. The mixture was stirred for 6 hours at room temperature. Ether (400 mL) was added. The resulting solids were collected by filtration, washed with ether and suction dried to afford 12.06 g of a bright mustard yellow solid. (93% yield). ICP showed 18.2% sulfur and 6.62% phosphorus (calculated 22% sulfur and 7.1% phosphorus).

Synthesis of Cyclododecasulfur.

Dichloromethane (100 mL) was added to a round bottom flask. Bromine (2.83 g, 17.7 mmol, 2.0 eq) in 50 mL dichloromethane was added. [PPh$_4$]$_2$[Zn(S$_6$)$_2$] (10 g, 8.86 mmol, 1.0 eq) was added all at once. There was an exotherm from 20° C. to 29° C. The bromine color disappeared immediately. The mixture was filtered to remove solids that strongly adhered to the filter paper and could not be removed. Yellow solids crystallized out of the filtrate. The filtrate was concentrated on a rotovap and the resulting solids were stirred overnight in methanol to remove impurities. The remaining solids were collected by filtration, washed with methanol and suction dried to afford 2.34 g of material (69% yield based on [PPh$_4$]$_2$[Zn(S$_6$)$_2$]). UQ showed the material to be 99.9% sulfur, 0.02% zinc and 0.05% bromine. Raman showed only a cyclododecasulfur compound.

Example 8

Comparison of melting points of cyclododecasulfur materials. Several batches of purified cyclododecasulfur of the present invention were prepared following the procedures exemplified by Examples 1 and 2. Each final purified material was analyzed by Raman, Uniquat® or ICP, and the melt point onset temperature was measured using DSC as described above. The results are set forth in Table 8 below along with "control" cyclododecasulfur melt points extrapolated from reported data measured at a DSC heat rate of 10° C./min, 5° C./min, and 2.5° C./min in Steudel, R.; Eckert, B., "Solid Sulfur Allotropes", Topics in Current Chemistry (2003).

TABLE 8

| sample | melting point, ° C. |
|---|---|
| invention batch 1 | 166.0 |
| invention batch 2 | 156.0 |
| invention batch 3 | 159.3 |
| invention batch 4 | 158.6 |
| invention batch 5 | 162.4 |
| invention batch 6 | 164.0 |
| invention batch 7 | 161.5 |
| control | 153.5 |

As shown above, the cyclododecasulfur compound of the present invention exhibits a melt point onset materially and unexpectedly higher than prior art cyclododecasulfur compounds. Observed variations in melt point for the present invention were expected due to degree of impurities in the samples as detected by Raman.

Example 9

Purification of Crude Cyclododecasulfur. Crude cyclododecasulfur was prepared as in Example 1 from (TMEDA)Zn(S$_6$) complex and bromine was found to contain 1.9 wt % zinc and 0.5 wt % bromine by ICP, and cyclooctasulfur and polymeric sulfur by Raman. The melt point onset temperature was measured as 132° C. using DSC as described above. Two grams of this crude cyclododecasulfur was added to 8 grams of p-xylene and heated to 115° C., with mixing, for one hour. The remaining solids then allowed to settle to the bottom of the container and the liquid was decanted off, while maintaining the temperature at 115° C. The solids were cooled to 50° C., and re-slurried with 15 grams of acetone, allowed to settle, and then the liquid was decanted off. The acetone slurry step was repeated two more times to ensure removal of p-xylene. A dilute solution of aqueous hydrochloric acid was prepared by mixing 0.22 grams of 37 wt % aqueous hydrochloric acid with 14.78 grams of demineralized water. The solid material from the acetone reslurry steps above was mixed with the dilute aqueous hydrochloric acid and held at 40° C. for one hour. Several drops of acetone, equivalent to about 10% of the total mixture, were added to the solids-hydrochloric acid mixture to prevent aggregation and aid in dispersion of the sulfur material into the solution. The vessel was vented to allow the escape of generated gases. After gas evolution stopped, the solids were allowed to settle and the liquid was decanted off. The remaining solids were slurried with 15 grams of acetone, allowed to settle, and the liquid removed. The acetone wash step was repeated two more times. After the final decantation, additional acetone was removed by vacuum filtration on a Buchner funnel equipped with filter paper. The solids from the Buchner funnel were reslurried-settled-decanted twice, each time with 15 grams of carbon disulfide. After the final decantation, additional carbon disulfide was removed by vacuum filtration on a Buchner funnel equipped with filter paper. The purified cyclododecasulfur material was dried at 40° C. under vacuum. After drying, a total of 1.55 g of purified cyclododecasulfur was recovered at a yield of 78% of the original crude cyclododecasulfur. XRD showed no detectable cyclooctasulfur (detection limit of 1%), while Raman showed no detectable cyclooctasulfur or polymeric sulfur. As calculated from ICP analysis, zinc and bromine levels in the purified cyclododecasulfur were reduced by 97% and 94% compared to the levels in the original crude cyclododecasulfur. The melting point onset temperature was found by DSC (20° C./min ramp rate) as 158.7° C.

Example 10

Purification of crude cyclododecasulfur by heating and crystallizing from para-xylene. Crude cyclododecasulfur was prepared as in Example 1, from (TMEDA)Zn($S_6$) complex and bromine, and was found to contain 1.9 wt % zinc and 0.5 wt % bromine by ICP, and cyclooctasulfur and polymeric sulfur by Raman. The melt point onset temperature was measured as 132° C. using DSC as described above. 7.53 grams of this crude cyclododecasulfur were added to a 1.5-liter jacketed glass vessel fitted with a 1 micron glass frit plate in the bottom of the vessel, and a mechanical agitator. 1504.45 grams of p-xylene were added to the fritted glass vessel and the mixture of crude cyclododecasulfur and p-xylene was heated to 115° C., with mixing, for thirty minutes. The contents of the vessel were pulled by vacuum through the fritted filter into a second 1.0-liter jacketed glass vessel fitted with a mechanical agitator. The contents of the 1.0-liter vessel were cooled to 18° C., with agitation. As the solution cooled, a large crop of light yellow crystals was seen to form. After a one-hour hold time, the slurry was drained onto a fritted filter covered with 1 micron filter. The yellow crystals were freed of liquid by vacuum filtration, and found to weigh 2.97 grams. The heat treatment and recrystallization procedure described above were found to produce cyclododecasulfur crystals of greater than 99.9% purity by UniQuant analysis. The solids from the filtration step were split into three fractions and each portion washed with either 20 grams of carbon disulfide, acetone, or p-xylene. The three washed samples were dried overnight at room temperature in a vacuum oven set at 0.017 MPa (absolute) and melting points were determined by DSC. Photomicrographs of each dried sample were taken to determine crystal habit and a rough particle size range. Results are given in Table 10.

TABLE 10

| Wash Solvent | DSC melt Point, ° C. | Crystal habit | particle size range |
|---|---|---|---|
| Carbon disulfide | 162.0 | agglomerates | <150 micron |
| Acetone | 161.5 | rods | <100 micron |
| p-xylene | 161.6 | rods | <100 micron |

Example 11

Purification of crude cyclododecasulfur by heating and crystallizing from chlorobenzene. Crude cyclododecasulfur was prepared as in Example 1, from (TMEDA)Zn($S_6$) complex and bromine, and was found to contain 1.9 wt % zinc and 0.5 wt % bromine by ICP, and cyclooctasulfur and polymeric sulfur by Raman. The melt point onset temperature was measured as 132° C. using DSC as described above. 7.47 grams of this crude cyclododecasulfur were added to a 1.5-liter jacketed glass vessel fitted with a 1 micron glass frit plate in the bottom of the vessel, and a mechanical agitator. 1499.7 grams of chlorobenzene were added to the fritted glass vessel and the mixture of crude cyclododecasulfur and chlorobenzene was heated to 115° C., with mixing, for thirty minutes. The contents of the vessel were pulled by vacuum through the fritted filter into a second 1.0-liter jacketed glass vessel fitted with a mechanical agitator. The contents of the 1.0-liter vessel were cooled to 18° C., with agitation. As the solution cooled, a large crop of light yellow crystals was seen to form. After a one-hour hold time, the slurry was drained onto a fritted filter covered with a 1 micron filter. The yellow crystals were freed of liquid by vacuum filtration, and found to weigh 3.75 grams. The heat treatment and recrystallization procedure described above were found to produce cyclododecasulfur crystals of greater than 99.9% purity by UniQuant analysis. The solids from the filtration step were split into three fractions and each portion washed with either 20 grams of carbon disulfide, acetone, or chlorobenzene. The three washed samples were dried overnight at room temperature in a vacuum oven set at 0.017 MPa (absolute) and melting points were determined by DSC. Photomicrographs of each dried sample were taken to determine crystal habit and a rough particle size range. Results are given in Table 11.

TABLE 11

| Wash Solvent | DSC melt Point, ° C. | Crystal habit | particle size range |
|---|---|---|---|
| Carbon disulfide | 162.67 | agglomerates | <250 micron |
| Acetone | 161.03 | rods | <100 micron |
| Chlorobenzene | 161.13 | rods | <100 micron |

Example 12

Purification of cyclododecasulfur by heating, sedimentation of zinc, and crystallizing. Four liters of chlorobenzene was added to a six-liter jacketed glass processing vessel fitted with a pitch-blade mechanical agitator, nitrogen purge, cooling water condenser, and heating bath for circulation of temperature-controlled oil through the vessel jacket. The circulating oil bath was adjusted to bring the processing vessel to an internal temperature of 115° C. Five hundred grams of crude $S_{12}$ as produced in Example 17 below were added into the processing vessel while stirring at about 300 rpm. The crude $S_{12}$ comprised 1.3 wt % Zn, 0.82 wt % Br, and the remainder S by Uniquant elemental analysis. The resulting slurry was maintained at 115° C. with stirring for 30 minutes. The processing vessel was then cooled to room temperature (about 20° C.) while stirring.

Once at room temperature, the agitation was stopped and larger, denser sulfur and zinc particles settled rapidly to the bottom of the processing vessel. Smaller, less dense, more buoyant, gray-green zinc particles settled slowly and largely remained suspended. The gray-green supernatant with suspended zinc particles was removed from the processing vessel by vacuum suction. Care was taken to ensure that the main sulfur cake was largely undisturbed. The liquid removed from the processing vessel was passed through a 5 micron filter paper, depositing gray solids. The resulting filtrate was clear yellow in color. The yellow filtrate was returned to the six-liter processing vessel containing the sulfur cake. At room temperature, agitation was started to re-suspend the settled solids. Agitation was again stopped to allow sedimentation into a sulfur cake and a lighter gray-green supernatant with suspended particles. This agitation/sedimentation/filtration cycle was repeated 4 times until the resulting supernatant was no longer greenish, but clear yellow in color. The zinc-rich solids collected on the filter were dried under vacuum overnight at 50° C. These dried solids were found to weigh 23.8 grams.

When no more light zinc particles remained suspended in the supernatant upon settling, the agitation was started to re-suspend the settled sulfur-rich solids. The suspended sulfur-rich solids were pulled out of the processing vessel by vacuum and passed through a 5 micron filter paper, depositing light yellow and gray solids. These solids were returned to the processing vessel and four liters of pure chlorobenzene were added. At room temperature, agitation was started to re-suspend the settled solids. Agitation was stopped to allow sedimentation into a dense gray zinc layer of heavy particles, with an upper layer of yellow sulfur particles, and a faint yellow supernatant with suspended sulfur particles. The faint yellow supernatant with suspended sulfur particles was removed from the processing vessel by vacuum suction. Care was taken to ensure that the zinc layer was largely undisturbed. The liquid removed from the processing vessel was passed through a 5 micron filter paper, depositing yellow sulfur solids. The resulting filtrate was returned to the processing vessel. The agitator was started to re-slurry the cake, and then stopped to allow settling of the heaviest zinc particles into a first zinc layer, with an upper layer of sulfur. Again suspended sulfur particles were removed by vacuum and filtered, with the filtrate returned to the processing vessel. This agitation/sedimentation/filtration cycle was repeated 5 times, gradually removing all of the sulfur particles until only a predominantly zinc layer remained. This final zinc layer was then removed from the processing vessel and was found to weigh 14.23 grams. The sulfur solids collected on the filter were dried under vacuum overnight at 50° C. These dried solids were found to weigh 350.69 grams (70% recovery of the original crude $S_{12}$ fed). Elemental analysis by the ICP method indicated 0.61 wt % Zn, 0.12 wt % Br, and the remainder sulfur. Raman showed only the presence of cyclododecasulfur. Melting point was determined to be 156.4° C. by DSC at a heat rate of 20° C./min.

The cyclododecasulfur product produced by the sedimentation step above was further processed by crystallization. 12 grams of the cyclododecasulfur was added to a 1.5-liter jacketed glass vessel fitted with a 1 micron glass frit plate in the bottom of the vessel, and a mechanical agitator. 1200 grams of chlorobenzene were added to the fritted glass vessel and the mixture of crude cyclododecasulfur and chlorobenzene was heated to 115° C., with mixing, for thirty minutes. The contents of the vessel were pulled by vacuum through the fritted filter into a second 1.0-liter jacketed glass vessel fitted with a mechanical agitator. The contents of the 1.0-liter vessel were cooled to 18° C., with agitation. As the solution cooled, a large crop of light yellow crystals was seen to form. After a 30-minute hold time, the slurry was drained onto a fritted filter covered with 1 micron filter paper. The filtrate liquid was added back to the 1.5-liter vessel and reheated to dissolve additional $S_{12}$, followed by draining of the supernatant into the 1-liter vessel, chilling to form crystals, and filtration. This process was repeated until no more $S_{12}$ could be dissolved into the chlorobenzene. The combined crop of light yellow crystals were freed of liquid by vacuum filtration and washed with 200 grams of acetone. The washed sample was dried overnight at room temperature in a vacuum oven set at 0.017 MPa (absolute). The melting point of the dried crystallized solids (10.0 grams) was determined by DSC as 159.5° C. The sample was found to be 99.85 wt % sulfur, 0.112 wt % Zn, and 0.0014 wt % Br by Uniquant.

Example 13

Purification of crude cyclododecasulfur by heating and crystallizing from chlorobenzene. Crude cyclododecasulfur from Example 17 (500 grams) was added to a 6-liter jacketed glass vessel fitted with a 1-micron glass frit plate in the bottom of the vessel, and a mechanical agitator. 4400 grams of chlorobenzene were added to the fritted glass vessel and the mixture of crude cyclododecasulfur and chlorobenzene was heated to 115° C., with mixing, for thirty minutes. The contents of the vessel were pulled by vacuum through the fritted filter into a second lower 6.0-liter jacketed glass vessel fitted with a mechanical agitator. The contents of the lower 6.0-liter vessel were cooled to 18° C., with agitation. As the solution cooled, a large crop of light yellow crystals was seen to form. After a one-hour hold time, the slurry was drained onto a fritted filter covered with a 1-micron filter. The filtrate was returned to the upper vessel, reheated to 115° C. to dissolve more $S_{12}$, and dropped to the lower vessel, and cooled to 18° C. to produce additional crystals. This process was repeated twenty times until no more crystals were seen to form upon cooling of the lower vessel. The yellow crystals on the fritted filter were freed of liquid by vacuum filtration. The solids from the filtration step were washed with acetone. The washed sample was dried overnight at room temperature in a vacuum oven set at 0.017 MPa (absolute). The dried sample was found to weigh 350.69 grams, with a melting point determined by DSC as 162.1° C. The sample was found to be greater than 99.9 wt % sulfur by Uniquant, and greater than 99% cyclododecasulfur by XRD analysis.

Example 14

Synthesis of (TMEDA)Zn($S_6$) with or without water addition. Tetramethyl ethylenediamine (TMEDA), (2042 grams, 85 wt %, 99% pure, reagent plus grade) and methanol (360 grams, 15 wt %) were added to a 6 L, 4-neck jacketed glass reactor equipped with a mechanical stirrer (reaching closely to the vessel walls), thermocouple, $N_2$ bubbler, and water condenser. The system was purged with nitrogen and the temperature of the mixture was adjusted to 22° C. Freshly ground cyclooctasulfur powder (673 grams, ~90% pure) was added over a few minutes while maintaining a stirring speed of 425-450 rpm. To this suspension, metallic zinc (207 grams, 3.1 moles, <10 μm particle size, 98% pure) was added over five minutes while maintaining the same stirring speed. A brown solution resulted with some greenish precipitate after heating the reaction mixture for 2 hours at 86° C. This indicated that the reaction failed to produce the desired (TMEDA)Zn($S_6$) complex. At this point, 78 g of water was added to the reaction and the resulting mixture was heated to 86° C. for an additional 2 hours and yellow precipitate of (TMEDA)Zn($S_6$) formed. At the end of the reaction time, the flask was cooled to room temperature, the agitator was turned off, and free liquid was removed by vacuum extraction. Methanol (2000 ml) was added to the flask to create slurry and agitated for one hour. The resulting slurry was then filtered on a vacuum Buchner filter (1 micron paper) and washed with two portions of 600 ml each of methanol. The solids were removed from the filter and dried overnight in a vacuum oven set at 50° C. and 0.1 MPa. The corresponding yield was near quantitative, with 1087 grams of metallasulfur derivative (TMEDA)Zn(S$_6$) complex, recovered at 97.5% purity as measured by NMR spectroscopy. Similar yields and purity were uniformly achieved in multiple runs under same reaction conditions. Addition of water consistently produced (TMEDA)Zn(S$_6$) complex in high yields and purity even with low grade TMEDA.

Example 15

Large-scale synthesis of (TMEDA)ZnS$_6$—The following procedure and equipment were used produce eleven batches of (TMEDA)Zn(S$_6$). Details are given below for Batch 1, with reference to Table 15 for specific differences for the other ten batches. Tetramethyl ethylenediamine (TMEDA), (10590.0 grams, 99% pure, reagent plus grade), methanol (1869 grams), and demineralized water (248 grams, 13.77 moles) were added to a nitrogen-purged 22-liter, 316L stainless steel reactor equipped with a mechanical pitched blade agitator, steam jacket, N$_2$ purge, and 2.54 cm×30 cm 316L stainless steel water-jacketed condenser. Steam was added to the reactor jacket to adjust the internal temperature to 25 celsius and agitation was set at 250 rpm. Freshly ground cyclooctasulfur powder (2387 grams, 74.59 moles, obtained from grinding greater than 99% pure cyclooctasulfur flake) was added over ten minutes while maintaining stirring at 250 rpm. Agitation was increased to 350 rpm and metallic zinc (734 grams, 11.23 moles, <10 µm particle size, 0.98% pure) was added over ten minutes while maintaining stirring at 350 rpm. Agitation was increased to 375 rpm and the resulting mixture was then heated slowly to 86° C. Vaporous material (mostly methanol) began to boil from the reactor at about 75° C., was condensed in the stainless steel condenser and returned continuously to the reactor. The reactor temperature was maintained at 87.8° C., and the reactor contents agitated at 375 rpm for three hours. At the end of the reaction time, the reactor was cooled to room temperature, the agitator was set to 100 rpm, and the reactor contents were drained through the bottom valve of the reactor into a polyethylene carboy. An additional four liters of fresh methanol was added to the reactor, agitation was increased to 150 rpm, and then the reactor contents were drained into the same carboy. A 36 cm×36 cm metal nutsche with a 5 micron polypropylene cloth, vacuum receiver flasks, and vacuum system was prepared to receive the crude (TMEDA)Zn(S$_6$) from the reaction step. The reaction effluent slurry was agitated and poured onto the nutsche cloth surface and drained of liquid by filtration under vacuum (0.025 to 0.06 MPa). The solids on the nutsche were washed with approximately 40 liters of methanol to remove residual TMEDA and unreacted sulfur. The washed solids were removed from the nutsche cloth, spread out on a large metal tray, and dried for 24 hours in a vacuum oven set at 55° C. and 0.025 to 0.06 MPa. The weight of dried metallasulfur derivative (TMEDA)Zn(S$_6$) complex was determined to be 3837.6 grams, recovered at 97.4% purity as measured by NMR spectroscopy. The molar yield on zinc metal was 89.2%. The average purity for batches 1-4 and 6-11 was 95.4%.

TABLE 15

| | Batch # | | | | | | | | | | |
|---|---|---|---|---|---|---|---|---|---|---|---|
| | 1 | 2 | 3 | 4 | 5 | 6 | 7 | 8 | 9 | 10 | 11 |
| Sulfur form | P | P | P | P | F | P | P | P | P | P | P |
| Sulfur, grams | 2387 | 2723 | 2724 | 2723 | 2723 | 2723 | 2723 | 2723 | 2723 | 2723 | 2723 |
| Zn dust, grams | 734 | 837 | 837 | 837 | 837 | 837 | 837 | 837 | 837 | 837 | 837 |
| TMEDA, grams | 10590 | 11313 | 11314 | 12020 | 12020 | 12020 | 12020 | 12020 | 12020 | 12020 | 12020 |
| MeOH, grams | 1869 | 2828 | 2828 | 2121 | 2121.3 | 2121 | 2121 | 2121 | 2121 | 2121.1 | 2121 |
| Water, grams | 248 | 282 | 282 | 282 | 282.1 | 282 | 282 | 282 | 282 | 282 | 282 |
| Rxn time, hrs | 3 | 3 | 3 | 3 | 4 | 3 | 3 | 3 | 3 | 3 | 3 |
| Hold temp, ° C. | 87.6 | 90 | 94 | 90.1 | 85.9 | 86.5 | 86.1 | 86.2 | 85.3 | 85 | 86.2 |
| Product Mass, g | 3837.6 | 3333.4 | 4313.4 | 4317.4 | 4318 | 4216.8 | 4258 | 4211.3 | 3975.1 | 4389.4 | 4214.9 |
| NMR purity, wt % | 97.4% | 94.0% | 95.8% | 96.4% | 29.4% | 96.3% | 96.4% | 93.7% | 95.6% | 95.8% | 93.2% |
| Zn Molar yield | 89.2% | 65.5% | 86.4% | 87.1% | 26.6% | 84.9% | 85.9% | 82.5% | 79.5% | 88.0% | 82.2% |

P = powder
F = flake

Example 16

Large-scale preparation of cyclododecasulfur from bromine and (TMEDA)ZnS6 complex. A jacketed glass-lined 1893-liter steel reactor fitted with two pitched blade turbine impellers, glycol cooling fluid on the jacket, nitrogen purge system, solids charging funnel, and pumped addition line was used to produce crude cyclododecasulfur from bromine and (TMEDA)ZnS$_6$ produced in Example 15. Chorobenzene (>99 wt % purity, 355.3 kilograms) was charged to the reactor, stirred at 100 rpm, and cooled overnight to about −4.6° C. Dried Batches #1 (3776.3 grams), #2 (3308.0 grams), #3 (4297 grams), and part of #4 (1900 grams) of (TMEDA)ZnS$_6$ prepared in Example 15 were added through the solids charging funnel while maintaining agitation. An additional six kilograms of chlorobenzene was poured through the solids funnel to wash residual solids into the reactor. Agitation was increased to 150 rpm, and previously prepared chlorobenzene/bromine solution (60 kg chlorobenzene, 5497.6 grams bromine, cooled to room temperature) was pumped into the reactor via the addition line over the course of one hour. During the addition step, glycol cooling flow to the reactor jacket was maintained, and the reactor temperature rose to about 4.5° C., indicating reaction of the bromine with the (TMEDA)ZnS$_6$ complex. The reactor contents were stirred and cooled for 30 minutes, during which the reactor internal temperature dropped to 2.0° C. The valve on the bottom of the reactor was opened and the contents were gravity fed to a stainless steel basket centrifuge (fitted with a 5-micron polypropylene filter cloth) for filtration of the produced crude cyclododecasulfur solids. The 1893-liter reactor was then charged with 420 liters of acetone to re-slurry any residual solids. This acetone slurry was then gravity fed to the centrifuge and passed through the solid cake of crude cyclododecasulfur crystals. The centrifuge cake was further washed with 105 liters of acetone and centrifuged for additional three hours to remove residual liquids. The cake was removed, recovered from the filter cloth, and found to weigh 14.75 kg with a moisture content of 65.7%. The wet solids were placed in stainless steel pans and dried for 17 hours in a vacuum oven at 50° C. and 0.067 MPa (absolute). The final weight of dry crude cyclododecasulfur thus produced weighed 5.05 kg, with a moisture content of 0.33 wt %.

Example 17

Large-scale preparation of cyclododecasulfur from bromine and (TMEDA)ZnS$_6$ complex. A jacketed glass-lined 1893-liter steel reactor fitted with two pitched blade turbine impellers, glycol cooling fluid on the jacket, nitrogen purge system, solids charging funnel, and pumped addition line was used to produce crude cyclododecasulfur from bromine and (TMEDA)ZnS$_6$ produced in Example 15. Chorobenzene (>99 wt % purity, 711.5 kilograms) was charged to the reactor, stirred at 100 rpm, and cooled overnight to about −4.4° C. Dried Batches #6 through #11 of (TMEDA)ZnS$_6$ (25.2 kg), prepared in Example 15 were added through the solids charging funnel while maintaining agitation. An additional six kilograms of chlorobenzene was poured through the solids funnel to wash residual solids into the reactor. Agitation was increased to 150 rpm, and previously prepared chlorobenzene/bromine solution (120 kg chlorobenzene, 10.2 kilograms bromine, cooled to room temperature) was pumped into the reactor via the addition line over the course of one hour. During the addition step glycol cooling flow to the reactor jacket was maintained, and the reactor temperature rose to about 3.0° C., indicating reaction of the bromine with the (TMEDA)ZnS$_6$ complex. The reactor contents were stirred and cooled for 20 minutes, during which the reactor internal temperature dropped to 2.0° C. The valve on the bottom of the reactor was opened and the contents were gravity fed to a stainless steel basket centrifuge (fitted with a 5-micron polypropylene filter cloth) for filtration of the produced crude cyclododecasulfur solids. The 1893-liter reactor was then charged with 840 liters of acetone to re-slurry any residual solids. This acetone slurry was then gravity fed to the centrifuge and passed through the solid cake of crude cyclododecasulfur crystals. The centrifuge cake was further washed with 212 liters of acetone and centrifuged for an additional five hours to remove residual liquids. The cake was removed, recovered from the filter cloth, and found to weigh 12.9 kg with a moisture content of 27.6%. The wet solids were placed in stainless steel pans and dried for 24 hours in a vacuum oven at 50° C. and 0.067 MPa (absolute). The final weight of dry crude cyclododecasulfur thus produced weighed 9.35 kg, with a moisture content of 0.30 wt %.

Example 18

Preparation of (TMEDA)Zn(S$_6$) with addition of water. Tetramethyl ethylenediamine (TMEDA), (2042 grams, 85 wt %, 99% pure, reagent plus grade), methanol (360 grams, 15 wt %), and water (78 grams) were added to a 6 L, 4-neck jacketed glass reactor equipped with two mechanical pitched blade agitators (reaching closely to the vessel walls), thermocouple, N$_2$ bubbler, and water condenser. The system was purged with nitrogen and the temperature of the mixture was adjusted to 22° C. Freshly ground cyclooctasulfur powder (673 grams, greater than 99% pure) was added over five minutes while maintaining a stirring speed of 425-450 rpm. To this suspension, metallic zinc (207 grams, 3.1 moles, <10 μm particle size, ≥98% pure) was added over five minutes while maintaining the same stirring speed. The greenish yellow mixture was then slowly heated to 86° C. and agitated for 2 hours, or until yellow precipitate appeared. Once the color turned yellow, the mixture was heated with stirring for an additional one hour. At the end of the reaction time, the flask was cooled to room temperature, the agitator was turned off, and free liquid was removed by vacuum extraction. Methanol (2000 ml) was added to the flask to create slurry and agitated for one hour. The resulting slurry was then filtered on a vacuum Buchner filter (1 micron paper) and washed with two portions of 600 ml each of methanol. The solids were removed from the filter and dried overnight in a vacuum oven set at 50° C. and 0.1 MPa. The corresponding molar yield on zinc metal was 90.1%, with 1087 grams of metallasulfur derivative (TMEDA)Zn(S$_6$) complex recovered at 98% purity as measured by NMR spectroscopy. Similar yields and purity were uniformly achieved in multiple runs under same reaction conditions.

Example 19

Preparation of cyclododecasulfur compound (S$_{12}$) using chlorine (Cl$_2$) as an oxidizing agent. Chlorobenzene (25 mL) was added to a 100 mL, 3-neck glass flask equipped with a stir-bar, thermocouple, N$_2$ bubbler and stopper. To this flask, the zinc complex, (TMEDA)Zn(S$_6$) (2.12 g, 5.53 mmol, 97.5% pure) was added and the resulting slurry was cooled to 0° C. using an ice-water bath. Next, a stoichiometric amount of chlorine (1M solution in chlorobenzene, 5.5 mL, 5.53 mmol, 1.0 eq) was introduced to the flask and the resulting mixture was stirred for 15 minutes, filtered, washed with chlorobenzene and suctioned dry. The solids were slurried in THF (200 mL), filtered, and suctioned dry. The resultant solids were slurried in cold CS$_2$ (50 mL), filtered and suctioned dry to afford 0.65 g of a pale yellow solid (yield 61.3% based on sulfur in the zinc complex). Evaluation using the X-ray diffraction (XRD) method and Raman Spectroscopy showed a mixture containing cyclododecasulfur, cyclooctasulfur, and polymeric sulfur species.

Example 20

Preparation of halide-free cyclododecasufur compound (S$_{12}$) with a substoichiometric amount of bromine (Br$_2$) as an oxidizing agent. Chlorobenzene (300 mL) was added to a 1 L, 4-neck glass flask equipped with a magnetic stir-bar, dropping funnel, N$_2$ bubbler and stopper. To this flask, the zinc complex, (TMEDA)Zn(S$_6$) (30.07 g, 75.98 mmol, 94.5% pure) was added and the resulting slurry was cooled to 0° C. using an ice-water bath. Bromine (3.85 mL, 74.46 mmol, 0.98 eq) as oxidizing agent was charged into the dropping funnel containing 50 mL chlorobenzene and this solution was dropwise added to the flask over a period of ~15 minutes. The solution was stirred for 15 minutes, filtered, washed with chlorobenzene to remove residual zinc complex and suctioned dry. The solids were slurried in THF (500 mL), filtered, and suctioned dry. The resultant solids were slurried in cold CS$_2$ (200 mL), filtered and suctioned dry to afford 10.4 g of a pale yellow solid (yield 71.1% based on sulfur in the zinc complex). Evaluation using the UQ elemental analysis method showed the material to be 99.9% sulfur (cyclododecasulfur compound (S$_{12}$) plus sulfur polymer by Raman spectroscopy) and 148 parts per million (ppm) zinc. No bromine-containing impurity was detected by UQ elemental analysis.

Example 21

Solubility of cyclooctasulfur, cyclododecasulfur, and crystalline polymeric sulfur in carbon disulfide, chlorobenzene, and para-xylene. Fifty grams of p-xylene was added to each of three identical 100-milliliter jacketed glass vessels fitted with a circulating heating bath, cooling water condenser, magnetic stir bar and stir plate, and nitrogen purge. All vessels were heated to the desired temperature, and cyclooctasulfur, cyclododecasulfur (prepared as in Example 2), and unoiled commercial crystalline polymeric sulfur (Crystex™) was added in sufficient quantities to each of the glass vessels to allow undissolved solids to remain after dissolution and equilibration of the mixture. The equilibration period typically lasted 2 to 8 hours, during which the contents of the vessel were maintained at the desired temperature and stirred continuously. Upon equilibration, supernatant liquid was withdrawn from the vessels via a heated fritted glass pipette (heated to the same temperature as the solution). The supernatants were analyzed by Uniquant to determine sulfur content, indicating the solubility of the sulfur species at the vessel temperature. Similar experiments were conducted for carbon disulfide and chlorobenzene for each of the three solutes. Solubilities in weight % of solute in each solvent are summarized in Table 21.

TABLE 21

| Solvent | Temperature, ° C. | Cyclo-octasulfur | Cyclo-dodecasulfur | Polymeric Sulfur |
|---|---|---|---|---|
| P-xylene | 22 | 2.3 wt % | Not measured | BDL* |
| | 45 | 5.6 wt % | <0.05 wt % | BDL* |
| | 115 | 18.7 wt % | 0.4 wt % | Decomposes to $S_8$ |
| Cl-benzene | 22 | 2.4 wt % | Not measured | BDL* |
| | 45 | 6.2 wt % | 0.015 wt % | BDL* |
| | 115 | 21.7 wt % | 0.44 wt % | Decomposes to $S_8$ |
| $CS_2$ | 22 | 32 wt % | 0.2 wt % | BDL* |
| | 45 | 48 wt % | 0.5 wt % | BDL* |

*BDL = below detection limit

Example 22

Thermal decomposition of crystalline polymeric sulfur in p-xylene. The purpose of this experiment was to determine the rate that polymeric sulfur thermally decomposes into cyclooctasulfur in p-xylene. Polymeric sulfur is essentially insoluble in p-xylene, except when the polymer decomposes into cyclooctasulfur. Thus, the sulfur content in the p-xylene is a measure of the amount of polymeric sulfur that has decomposed to cyclooctasulfur. In this experiment, 50.32 grams of p-xylene were added to a 100-milliliter jacketed glass vessels fitted with a circulating heating bath, cooling water condenser, magnetic stir bar and stir plate, and nitrogen purge. The p-xylene was heated to 115° C. and 2.03 grams of unoiled commercial crystalline polymeric sulfur (Crystex™) was added while stirring. Periodically samples of the supernatant liquid were withdrawn from the vessel via a heated fritted glass pipette (heated to the same temperature as the solution). These supernatant samples were analyzed by Uniquant to determine sulfur content. The sulfur content was used to calculate the amount of polymeric sulfur remaining undissolved and undecomposed to cyclooctasulfur. After 60 and 75 minutes at 115° C., about 85% and essentially 100% respectively, of the polymeric sulfur had been converted into cyclooctasulfur.

Example 23

Thermal decomposition of cyclododecasulfur in p-xylene. The equipment and procedure used in Example 22 for measurement of the decomposition of polymeric sulfur was used to measure the decomposition of cyclododecasulfur in para-xylene. Two grams of purified cyclododecasulfur (produced by a procedure in the fashion of Example 2) was heated and stirred in 50.0 grams of p-xylene in a 100-milliliter jacketed glass vessels fitted with a circulating heating bath, cooling water condenser, magnetic stir bar and stir plate, and nitrogen purge. After 60, 75, and 120 minutes at 115° C., the content of sulfur in the p-xylene solvent was found by Uniquant to be about 0.4 wt % in each case, similar to the solubility of cyclododecasulfur in p-xylene at 115° C. (see Example 21). Upon cooling of the p-xylene, filtration, and drying of the recovered solids overnight in a vacuum oven at room temperature and 0.067 MPa (absolute), greater than 97% of the cyclododecasulfur input weight of solids was recovered. This material had a melting point of 161° C. by DSC, indicating high purity cyclododecasulfur product.

Example 24

Oxidation of (TMEDA)ZnS$_6$ by O2. O2 gas was bubbled into a suspension of (TMEDA)ZnS$_6$ (1.0 mmol) in water (30 mL) in the presence of ethylene diamine (4.0 mmol) at room temperature for 4 hours, resulting in a light yellow suspension. The suspension was filtered and washed with H$_2$O, acetone, and dichloromethane, and then dried in air to give a cyclododecasulfur-containing reaction mixture comprising cyclohexasulfur, cyclooctasulfur, and cyclododecasulfur, at a 50% sulfur yield.

Example 25

Oxidation of (TMEDA)ZnS$_6$ by H2O2. H2O2 (34 wt % in water) was added dropwise over 30 minutes to a suspension of (TMEDA)ZnS$_6$ (1.0 mmol) in water (30 mL) in the presence of ethylene diamine (4.0 mmol) at room temperature for 4 hours, resulting in a light yellow suspension. The suspension was filtered and washed with H$_2$O, acetone, and dichloromethane, and then dried in air to give a cyclododecasulfur-containing reaction mixture comprising cyclohexasulfur, cyclooctasulfur, and cyclododecasulfur, at a 70% sulfur yield.

Example 26

Oxidation of (TMEDA)ZnS$_6$ by SO$_2$Cl$_2$. SO$_2$Cl$_2$ (6.0 mmol) was added dropwise over 60 minutes to a suspension of (TMEDA)ZnS$_6$ (3.0 mmol) in dichloromethane (40 mL) at −78° C. The resulting solution was stirred for an additional hour at −78° C. Upon warming to 0° C. a light yellow suspension formed. The suspension was quenched with 5 ml of 1M HCL solution in 15 ml of H$_2$O. The quenched solution, was filtered and washed with H$_2$O, acetone, and dichloromethane, and then dried in air to give a cyclododecasulfur-containing reaction mixture comprising cyclododecasulfur, at a 40% sulfur yield.

Example 27

Purification of crude cyclododecasulfur by crystallizing from chlorobenzene. Crude cyclododecasulfur from Example 17 was heat treated and subjected to zinc sedimentation as in Example 12. This partially purified material was subjected to continuous dissolving and cooling crystallizing steps from chlorobenzene solvent to produce a purified $S_{12}$ product. The continuous dissolving-crystallizing apparatus comprised the following in counterclockwise flow order: a 15-liter jacketed glass dissolving vessel (steam heated) fitted with a 5 micron filter paper covered by a stainless steel screen and supported on a perforated Teflon plate in the bottom of the vessel, a mechanical agitator, cooling water condenser, upper solvent inlet port, and bottom flow valve; centrifugal pump (maximum 23 liter/min maximum flow rate); a cartridge filter fitted with a spiral wound glass-baked fiber element (0.75 micron, 0.046 m² area); a shell in tube heat exchanger comprising 20 meters of coiled 1.25 cm nominal diameter stainless steel tubing (process side) in a 5 cm stainless steel shell (cooling fluid side–chilled water coolant); a bag filter and housing fitted with 5 micron 0.1 m² area polypropylene woven filter; a 4 liter stainless steel mother liquor tank; a centrifugal pump (maximum 23 liter/min maximum flow rate); a shell in tube heat exchanger comprising 20 meters of coiled 1.25 cm nominal diameter stainless steel tubing (process side) in a 5 cm stainless steel shell (heating fluid side–steam heating); with outlet from the hot exchanger returning to the dissolving tank. All tubing connecting the dissolving vessel, cartridge filter, hot exchanger up to the process inlet of the cold exchanger was fitted with electrical heating tape to maintain the desired dissolution temperature. All tubing connecting the cold exchanger, mother liquor tank, to the inlet of the hot exchanger was fitted with foam insulation to maintain the desired dissolution temperature. Both the process fluid and inlet chilled water flow entered the cold exchanger at the top of the vessel (in tube and shell side respectively) to give co-current flow.

The dissolving tank was charged with 15 liters of chlorobenzene, solvent circulation was started at 5.4 liters/min. The steam flow to the hot exchanger and dissolving vessels and heat tapes were adjusted to maintain an average temperature of 106.5° C. at the process fluid inlet to the cold exchanger throughout the experiment. Chilled water flow was adjusted to maintain the process side outlet temperature of the cold exchanger at an average of 24.7° C. throughout the experiment. Once equilibrium temperatures as described above were reached in the process fluid loop, 50 grams of feed material (partially purified $S_{12}$ as described above) was added to the dissolving vessel, producing a yellow green slurry mixture. Within five minutes, light yellow crystals were seen to be collecting in the bag filter. After an additional 5-10 minutes, the dissolving tank became clear, indicating removal of $S_{12}$ and dark gray-green solids were seen on the filter paper. An additional 51 gram charge of feed material was added to the dissolving tank and the process repeated until the dissolving tank became clear again. Additional 50 gram charges of feed material were added and processed for a total charge of 302.34 grams. The flows were stopped and light yellow crystals emptied from the bag filter. Solvent-wet $S_{12}$ solids from the bag filter were washed with acetone to remove chlorobenzene and dried overnight at room temperature in a vacuum oven set at 0.017 MPa (absolute). The melting point of the dried $S_{12}$ crystalline product (243 grams) was determined by DSC as 162.1° C., with a purity greater than 99.9 wt % sulfur by Uniquant, with a Dv(50) of 41 microns by PSD analysis.

Example 28

Purification of crude cyclododecasulfur by impinging jet cooling crystallizing from chlorobenzene. Crude cyclododecasulfur was purified by a heat treating step as in Example 13, and was further processed in an impinging jet cooling crystallizing step to produce tailored particle size cyclododecasulfur crystals. The impinging jet apparatus comprised two agitated hot and cold glass jacketed 4-liter vessels, gear pumps for pumping fluid, a stainless steel impinging jet tee (dimensions: 2 mm inside diameter cool fluid inlet, 2 mm inside diameter hot fluid inlet, 5 mm outlet tubing), 1 micron filter paper on a fritted glass plate, and a glass filtrate collection vessel.

In a first experiment, 4.5 grams of heat-treated $S_{12}$ was dissolved in 1650 grams of chlorobenzene in the hot vessel at 110° C. The cold vessel was filled with chlorobenzene and chilled to -20° C. Once the $S_{12}$ had dissolved flow was started to the impinging jet tee at rate of 180 ml/min hot fluid and 360 ml/min cold fluid. Small light yellow crystals were observed to form immediately in the impinging jet outlet stream, and were filtered out on the 1 micron paper, and mother liquor collected in the filtrate tank. The outlet mixture stream of the impinging jet was found to have a temperature of 23° C. Solvent-wet $S_{12}$ solids from the filter paper were washed with acetone to remove chlorobenzene and dried overnight at room temperature in a vacuum oven set at 0.017 MPa (absolute). The dried crystals (4.1 grams) were submitted for particle size distribution. A second experiment was complete at identical conditions except changing the cold fluid flow to 540 ml/min. Outlet temperature was 12.5° C., with a dry crystal recovery of 4.2 grams. Results are given in Table 28 for both experiments.

TABLE 28

|  | Experiment 1 | Experiment 2 |
|---|---|---|
| Cold/hot flow ratio | 2/1 | 3/1 |
| Cold linear vel, m/s | 1.91 | 2.86 |
| Hot linear vel, m/s | 0.95 | 0.95 |
| Outlet T, ° C. | 23.3 | 12.5 |
| D[4, 3], microns | 80.9 | 35.9 |
| Dv(10), microns | 25.2 | 12.8 |
| Dv(50), microns | 66.9 | 31.7 |
| Dv(90), microns | 145 | 65.3 |

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method for the manufacture of cyclododecasulfur, comprising reacting a metallasulfur derivative with an oxidizing agent in a reaction zone to form a cyclododecasulfur-containing reaction mixture containing cyclododecasulfur, wherein the oxidizing agent is characterized by the formula:

X—X' wherein X and X' are the same or different and are selected from the group consisting of halogens or pseudohalogens.

2. The method of claim 1 wherein the metallasulfur derivative is characterized by the formula:

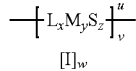

wherein
L is a monodentate or polydentate ligand species which may be the same or different when x>1;
x is the total number of ligand species and is from 0 to 6 inclusive;
M is a metal atom;
y is the total number of metal atoms and is from 1 to 4 inclusive;
S is a sulfur atom;
z is the number of sulfur atoms, and is from 1 to 12 inclusive;
u represents the charge of the metallasulfur derivative and may be from −6 to +6 inclusive;
v is the number of metallasulfur derivative units in an oligomeric or polymeric structure;
I is an ionic atom or group and may be cationic or anionic; and w is the number of cationic or anionic atoms or groups, as required to provide charge neutrality.

3. The method of claim 1, wherein the stoichiometric ratio of the oxidizing agent to the metallasulfur derivative is less than one equivalent of the oxidizing agent present for every two M-S bonds in the metallasulfur derivative.

4. The method of claim 1, wherein X and X' are one or more of chlorine and bromine.

5. The method of claim 1, wherein X and X' are chlorine.

6. The method of claim 1, wherein X and X' are bromine.

7. The method of claim 1, wherein X and X' comprise one or more of a cyanide, a thiocyanide, a sulfate, a thiosulfate, a sulfonate, or a thiosulfonate.

8. The method of claim 1, further comprising a step of reacting elemental sulfur with a sulfur templating agent to form the metallasulfur derivative prior to the step of reacting the metallasulfur derivative with the oxidizing agent.

9. The method of claim 8, wherein the reacting the elemental sulfur with a sulfur templating agent to form the metallasulfur derivative is carried out in the presence of water.

10. The method of claim 1, further comprising a step of isolating the cyclododecasulfur from the cyclododecasulfur-containing reaction mixture.

11. The method of claim 10, wherein the step of isolating the cyclododecasulfur from the cyclododecasulfur-containing reaction mixture comprises one or more steps chosen from dissolving, heat treating, drying, acid treating, solvent washing, crystallizing, and sedimentation.

12. The method of claim 10, wherein the step of isolating the cyclododecasulfur comprises treating the cyclododecasulfur with a solvent for the cyclododecasulfur to form a dissolution liquor.

13. The method of claim 10, further comprising removing metal and metal-containing compounds from the cyclododecasulfur by sedimentation of the metal and the metal-containing compounds.

14. The method of claim 1, further comprising isolating cyclododecasulfur by heating a cyclododecasulfur-containing mixture in the presence of a solvent to decompose and dissolve in the solvent impurities that are present.

15. The method of claim 1, further comprising isolating cyclododecasulfur by treating a cyclododecasulfur-containing mixture with an acid to remove any metal or metal-containing compounds that are present.

16. The method of claim 12, further comprising crystallizing cyclododecasulfur from the dissolution liquor.

17. A method for the manufacture of cyclododecasulfur, the method comprising:
(i) reacting cyclooctasulfur, tetramethylethylenediamine, and zinc to form a tetramethylethylenediamine/Zn(S$_6$) complex; and
(ii) reacting the complex with an oxidizing agent, wherein the oxidizing agent is characterized by the formula:

wherein X and X' are the same or different and are selected from the group consisting of halogens or pseudohalogens.

18. The method of claim 17, wherein the step of reacting the cyclooctasulfur, the tetramethylethylenediamine, and the zinc to form a tetramethylethylene-diamine/Zn(S$_6$) complex is carried out in the presence of water.

* * * * *